US008338113B2

(12) United States Patent
Guetta et al.

(10) Patent No.: US 8,338,113 B2
(45) Date of Patent: Dec. 25, 2012

(54) METHODS FOR DETECTING FETAL CELLS IN THE MATERNAL BLOOD

(75) Inventors: Esther Guetta, Ramat-Gan (IL); Gad Barkai, Ramat-Gan (IL); Liat Gutstein-Abo, Tel-Aviv (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 242 days.

(21) Appl. No.: 12/451,183

(22) PCT Filed: May 1, 2008

(86) PCT No.: PCT/IL2008/000598
§ 371 (c)(1),
(2), (4) Date: Mar. 15, 2010

(87) PCT Pub. No.: WO2008/132753
PCT Pub. Date: Nov. 6, 2008

(65) Prior Publication Data
US 2010/0173291 A1 Jul. 8, 2010

Related U.S. Application Data

(60) Provisional application No. 60/924,149, filed on May 1, 2007.

(51) Int. Cl.
*G01N 33/53* (2006.01)
*C12Q 1/68* (2006.01)
*C12N 5/07* (2010.01)
*C12N 5/073* (2010.01)

(52) U.S. Cl. .......... 435/7.2; 435/6.1; 435/6.12; 435/7.1; 435/7.21; 435/4; 435/325; 435/372

(58) Field of Classification Search .................. None
See application file for complete search history.

(56) References Cited

U.S. PATENT DOCUMENTS

| 5,858,649 | A | 1/1999 | Asgari et al. |
| 2005/0049793 | A1 | 3/2005 | Paterlini-Brechot |
| 2005/0124003 | A1 | 6/2005 | Atala et al. |
| 2006/0040305 | A1 | 2/2006 | Fejgin et al. |

FOREIGN PATENT DOCUMENTS

| EP | 1154016 | 11/2001 |
| WO | WO 90/06509 | 6/1990 |
| WO | WO 2006/018849 | 2/2006 |
| WO | WO 2008/132753 | 11/2008 |

OTHER PUBLICATIONS

Maldondo-Estrada et al. J. Immunological Methods. 2004. 286:21-34.*
Sjolin et al. Biochem J. 1994. 300: 325-330.*
Haynes et al. Electrophoresis. 1998. 19: 1862-1871.*
Gokmen-Polar et al. Cancer Research. 2001. 61: 1375-1381.*
Liu et al Clinical Immunology. 2004. 112: 225-230.*
Coleman et al. Drug Discovery Today. 2003. 8: 233-235.*
Saetre et al. Molecular Brain Research. 2004. 126: 198-206.*
Romisch et al. Blood Coagulation & Fibrinolysis. 1992. 3: 11-17.*
Response Dated Feb. 16, 2011 to Supplementary European Search Report and the European Search Opinion of Jul. 30, 2010 From the European Patent Office Re. Application No. 08738299.0.
Hawes et al. "A Morphologic Study of Trophoblast Isolated From Peripheral Blood of Pregnant Women", American Journal of Obstetrics and Gunaecology, 170: 1297-1300, 1994.
International Search Report and the Written Opinion Dated Jan. 9, 2009 From the International Searching Authority Re.: Application No. PCT/IL08/00598.
International Search Report Dated Jan. 9, 2009 From the International Searching Authority Re.: Application No. PCT/IL08/00598.
Written Opinion Dated Jan. 9, 2009 From the International Searching Authority Re.: Application No. PCT/I08/00598.
Bianchi et al. "Male Fetal Progenitor Cells Persist in Maternal Blood for as Long as 27 Years Postpartum", Proc. Natl. Acad. Sci. USA, 93: 705-708, Jan. 1996.
Blaschitz et al. "Antibody Reaction Patterns in First Trimester Placenta: Implications for Trophoblast Isolation and Purity Screening", Placenta, 21: 733-741, 2000. p. 734, Table 1, § 3, p. 735, § 5.
Daya et al. "The Use of Cytokeratin as a Sensitive and Reliable Marker for Trophoblastic Tissue", American Journal of Clinical Pathology, 95: 137-141, Feb. 1991. Abstract.
Guetta et al. "Analysis of Fetal Blood Cells in the Maternal Circulation: Challenges, Ongoing Efforts, and Potential Solutions", Stem Cells and Development, 13: 93-99, Feb. 2004. Abstract.
Guetta et al. "Hematopoietic Progenitor Cells as Targets for Non-Invasive Prenatal Diagnosis: Detection of Fetal CD34+ Cells and Assessment of Post-Delivery Persistence in the Maternal Circulation", Blood Cells, Molecules & Diseases, 30(1): 13-21, Jan.-Feb. 2003. Abstract.
Guetta et al. "Trophoblasts Isolated From the Maternal Circulation: In-Vitro Expansion and Potential Application in Non-Invasive Prenatal Diagnosis", Journal of Histochemistry & Cytochemistry, 53(3): 337-339, 2005.
King et al. "Cell Culture Models of Trophoblast II: Trophoblast Cell Lines—A Workshop Report", Placenta, Supplement A: Trophoblast Research, 21: S113-S119, 2000. p. S114, § 2.
Kirszenbaum et al. "Evidence for the Presence of the Alternatively Spliced HLA-G mRNA Forms in human Mononuclear Cells From Peripheral Blood and Umbilical Cord Blood", Human Immunology, 43(3): 237-241, Jul. 1995. Abstract.
Maldonado-Estrada et al. "Evaluation of Cytokeratin 7 as an Accurate Intracellular Marker With Which to Assess the Purity of Human Placental Villous Trophoblast Cells by Flow Cytometry", Journal of Immunological Methods, 286(1-2): 21-34, Mar. 2004.
Masada et al. "Levels of Annexin IV and V in the Plasma of Pregnant and Postpartum Women", Thrombosis and Haemostasis, 91(6): 1129-1136, Jun. 2004. Abstract.

(Continued)

*Primary Examiner* — Carla Myers

(57) ABSTRACT

Provided is a method of identifying a trophoblast by detecting in cells of a biological sample, with the proviso that the biological sample does not comprise a placental tissue, expression of a trophoblast marker selected from the group consisting of an annexin IV, a cytokeratin-7, a cytokeratin-8 and a cytokeratin-19; and classifying cells exhibiting expression of the trophoblast marker as trophoblasts. Also provided are methods of detecting a pregnancy in a subject, isolating trophoblasts from biological samples and prenatally diagnosing a conceptus using the identified trophoblasts.

16 Claims, 9 Drawing Sheets
(9 of 9 Drawing Sheet(s) Filed in Color)

OTHER PUBLICATIONS

Oudejans et al. "Circulating Trophoblast in Maternal Blood", Prenatal Diagnosis, 23: 111-116, 2003.
Tamai et al. "Cytokeratins 8 and 19 in the Mouse Placental Development", The Journal of Cell Biology, 151(3): 563-572, Oct. 30, 2000.
Tempfer et al. "Placental Expression and Serum Concentrations of Cytokeratin 19 in Preeclampsia", Obstetrics Gynecology, 95(5 Part 1): 677-682, May 2000.
Troeger et al. "Approximately Half of the Erythroblasts in Maternal Blood Are of Fetal Origin", Molecular Human Reproduction, 5(12): 1162-1165, 1999.
Van Wijk et al. "HLA-G Expression in Trophoblast Cells Circulating in Maternal Peripheral Blood During Early Pregnancy", American Journal of Obstetrics and Gynecology, 184(5): 991-997, Apr. 2001.
Vona et al. "Enrichment, Immunomorphological, and Genetic Characterization of Fetal Cells Circulating in Maternal Blood", American Journal of Pathology, 160(1): 51-58, 2001.
Yamamoto et al. "Cloning and Sequence of cDNA for Human Placental Cytokeratin 8. Regulation of the mRNA in Trophoblastic Cells by cAMP", Molecular Endocrinology, 4(3): 370-374, 1990. Abstract.

International Preliminary Report on Patentability Dated Jan. 28, 2010 From the International Bureau of WIPO Re.: Application No. PCT/IL2008/000598.
Supplementary European Search Report and the European Search Opinion Dated Jul. 30, 2010 From the European Patent Office Re. Application No. 08738299.0.
Eldering et al. "Presence of Lipocortins I and IV, But Not II and VI, in Human Platelets", FEBS Letters, XP025652271, 318(3): 231-234, Mar. 8, 1993. Abstract, p. 231, col. 1, § 2, Fig.1.
Koumantaki et al. "Microsatellite Analysis Provides Efficient Confirmation of Fetal Trophoblast Isolation From Maternal Circulation", Prenatal Diagnosis, XP008072425, 21: 566-570, Jan. 1, 2001. Abstract, p. 568, col. 1, § 2.
Masuda et al. "Levels of Annexin IV and V in the Plasma of Pregnant and Postpartum Women", Thrombosis and Haemostasis, XP008124154, 91(6): 1129-1136, Jun. 2004. Abstract, p. 1134, col. 2, § 2.
Office Action Dated Oct. 6, 2011 From the Israeli Patent Office Re. Application No. 201759 and Its Translation Into English.

* cited by examiner

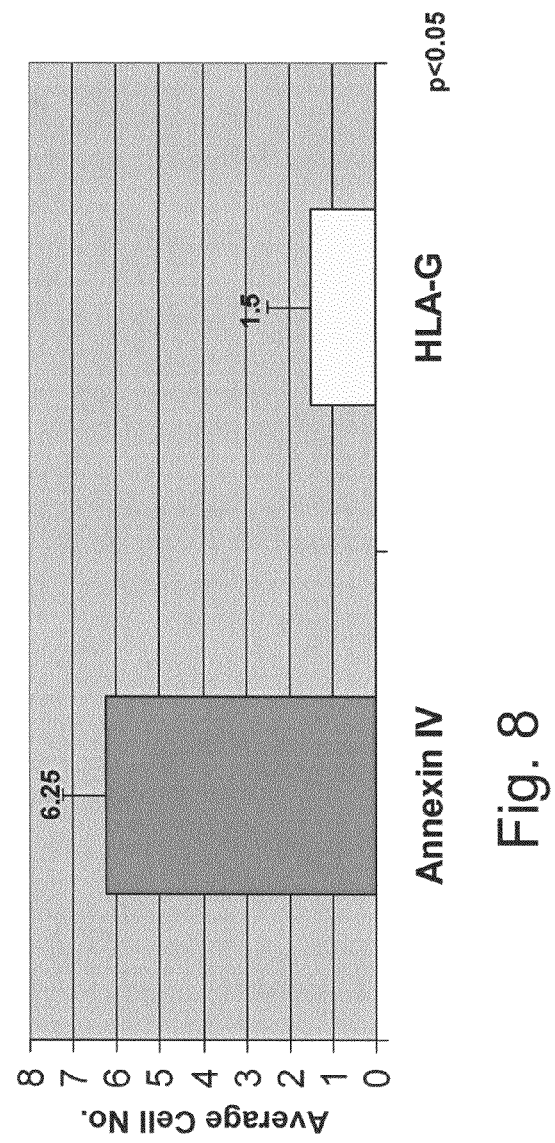

SEQUENCE LISTING

<160> NUMBER OF SEQ ID NOS: 24

<210> SEQ ID NO 1
<211> LENGTH: 469
<212> TYPE: PRT
<213> ORGANISM: Homo sapiens

<400> SEQUENCE: 1

Met Ser Ile His Phe Ser Ser Pro Val Phe Thr Ser Arg Ser Ala Ala
 1               5                  10                  15

Phe Ser Gly Arg Gly Ala Gln Val Arg Leu Ser Ser Ala Arg Pro Gly
            20                  25                  30

-continued

```
Gly Leu Gly Ser Ser Leu Tyr Gly Leu Gly Ala Ser Arg Pro Arg
         35                  40                  45
Val Ala Val Arg Ser Ala Tyr Gly Gly Pro Val Gly Ala Gly Ile Arg
 50                  55                  60
Glu Val Thr Ile Asn Gln Ser Leu Leu Ala Pro Leu Arg Leu Asp Ala
 65                  70                  75                  80
Asp Pro Ser Leu Gln Arg Val Arg Gln Glu Glu Ser Glu Gln Ile Lys
                 85                  90                  95
Thr Leu Asn Asn Lys Phe Ala Ser Phe Ile Asp Lys Val Arg Phe Leu
                100                 105                 110
Glu Gln Gln Asn Lys Leu Leu Glu Thr Lys Trp Thr Leu Leu Gln Glu
                115                 120                 125
Gln Lys Ser Ala Lys Ser Ser Arg Leu Pro Asp Ile Phe Glu Ala Gln
        130                 135                 140
Ile Ala Gly Leu Arg Gly Gln Leu Glu Ala Leu Gln Val Asp Gly Gly
145                 150                 155                 160
Arg Leu Glu Ala Glu Leu Arg Ser Met Gln Asp Val Val Glu Asp Phe
                165                 170                 175
Lys Asn Lys Tyr Glu Asp Glu Ile Asn His Arg Thr Ala Ala Glu Asn
                180                 185                 190
Glu Phe Val Val Leu Lys Lys Asp Val Asp Ala Ala Tyr Met Ser Lys
        195                 200                 205
Val Glu Leu Glu Ala Lys Val Asp Ala Leu Asn Asp Glu Ile Asn Phe
210                 215                 220
Leu Arg Thr Leu Asn Glu Thr Glu Leu Thr Glu Leu Gln Ser Gln Ile
225                 230                 235                 240
Ser Asp Thr Ser Val Val Leu Ser Met Asp Asn Ser Arg Ser Leu Asp
                245                 250                 255
Leu Asp Gly Ile Ile Ala Glu Val Lys Ala Gln Tyr Glu Glu Met Ala
                260                 265                 270
Lys Cys Ser Arg Ala Glu Ala Glu Ala Trp Tyr Gln Thr Lys Phe Glu
        275                 280                 285
Thr Leu Gln Ala Gln Ala Gly Lys His Gly Asp Asp Leu Arg Asn Thr
290                 295                 300
Arg Asn Glu Ile Ser Glu Met Asn Arg Ala Ile Gln Arg Leu Gln Ala
305                 310                 315                 320
Glu Ile Asp Asn Ile Lys Asn Gln Arg Ala Lys Leu Glu Ala Ala Ile
                325                 330                 335
Ala Glu Ala Glu Glu Arg Gly Glu Leu Ala Leu Lys Asp Ala Arg Ala
                340                 345                 350
Lys Gln Glu Glu Leu Glu Ala Ala Leu Gln Arg Gly Lys Gln Asp Met
        355                 360                 365
Ala Arg Gln Leu Arg Glu Tyr Gln Glu Leu Met Ser Val Lys Leu Ala
370                 375                 380
Leu Asp Ile Glu Ile Ala Thr Tyr Arg Lys Leu Leu Glu Gly Glu Glu
385                 390                 395                 400
Ser Arg Leu Ala Gly Asp Gly Val Gly Ala Val Asn Ile Ser Val Met
                405                 410                 415
Asn Ser Thr Gly Gly Ser Ser Gly Gly Gly Ile Gly Leu Thr Leu
                420                 425                 430
Gly Gly Thr Met Gly Ser Asn Ala Leu Ser Phe Ser Ser Ala Gly
        435                 440                 445
Pro Gly Leu Leu Lys Ala Tyr Ser Ile Arg Thr Ala Ser Ala Ser Arg
450                 455                 460
```

```
Arg Ser Ala Arg Asp
465

<210> SEQ ID NO 2
<211> LENGTH: 483
<212> TYPE: PRT
<213> ORGANISM: Homo sapiens

<400> SEQUENCE: 2

Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
            20                  25                  30

Ile Ser Ser Ser Ser Phe Ser Arg Val Gly Ser Ser Asn Phe Arg Gly
        35                  40                  45

Gly Leu Gly Gly Gly Tyr Gly Gly Ala Ser Gly Met Gly Gly Ile Thr
    50                  55                  60

Ala Val Thr Val Asn Gln Ser Leu Leu Ser Pro Leu Val Leu Glu Val
65                  70                  75                  80

Asp Pro Asn Ile Gln Ala Val Arg Thr Gln Glu Lys Glu Gln Ile Lys
                85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
        115                 120                 125

Gln Lys Thr Ala Arg Ser Asn Met Asp Asn Met Phe Glu Ser Tyr Ile
    130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
                165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
        195                 200                 205

Glu Leu Glu Ser Arg Leu Glu Gly Leu Thr Asp Glu Ile Asn Phe Leu
    210                 215                 220

Arg Gln Leu Tyr Glu Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
                245                 250                 255

Asp Ser Ile Ile Ala Glu Val Lys Ala Gln Tyr Glu Asp Ile Ala Asn
            260                 265                 270

Arg Ser Arg Ala Glu Ala Glu Ser Met Tyr Gln Ile Lys Tyr Glu Glu
        275                 280                 285

Leu Gln Ser Leu Ala Gly Lys His Gly Asp Asp Leu Arg Arg Thr Lys
    290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
                325                 330                 335

Asp Ala Glu Gln Arg Gly Glu Leu Ala Ile Lys Asp Ala Asn Ala Lys
            340                 345                 350

Leu Ser Glu Leu Glu Ala Ala Leu Gln Arg Ala Lys Gln Asp Met Ala
        355                 360                 365
```

```
Arg Gln Leu Arg Glu Tyr Gln Glu Leu Met Asn Val Lys Leu Ala Leu
    370                 375                 380

Asp Ile Glu Ile Ala Thr Tyr Arg Lys Leu Leu Glu Gly Glu Glu Ser
385                 390                 395                 400

Arg Leu Glu Ser Gly Met Gln Asn Met Ser Ile His Thr Lys Thr Thr
                405                 410                 415

Ser Gly Tyr Ala Gly Gly Leu Ser Ser Ala Tyr Gly Gly Leu Thr Ser
                420                 425                 430

Pro Gly Leu Ser Tyr Ser Leu Gly Ser Ser Phe Gly Ser Gly Ala Gly
            435                 440                 445

Ser Ser Ser Phe Ser Arg Thr Ser Ser Ser Arg Ala Val Val Val Lys
            450                 455                 460

Lys Ile Glu Thr Arg Asp Gly Lys Leu Val Ser Glu Ser Ser Asp Val
465                 470                 475                 480

Leu Pro Lys

<210> SEQ ID NO 3
<211> LENGTH: 400
<212> TYPE: PRT
<213> ORGANISM: Homo sapiens

<400> SEQUENCE: 3

Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Gly Ala Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
            115                 120                 125

His Tyr Tyr Thr Thr Ile Gln Asp Leu Arg Asp Lys Ile Leu Gly Ala
        130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Glu Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Glu Ile Ser Thr
    210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255
```

```
Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
            275                 280                 285

Leu Gln Met Ser Arg Ser Glu Val Thr Asp Leu Arg Arg Thr Leu Gln
            290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
            325                 330                 335

His Ile Gln Ala Leu Ile Ser Gly Ile Glu Ala Gln Leu Gly Asp Val
            340                 345                 350

Arg Ala Asp Ser Glu Arg Gln Asn Gln Glu Tyr Gln Arg Leu Met Asp
            355                 360                 365

Ile Lys Ser Arg Leu Glu Gln Glu Ile Ala Thr Tyr Arg Ser Leu Leu
            370                 375                 380

Glu Gly Gln Glu Asp His Tyr Asn Asn Leu Ser Ala Ser Lys Val Leu
385                 390                 395                 400

<210> SEQ ID NO 4
<211> LENGTH: 142
<212> TYPE: PRT
<213> ORGANISM: Homo sapiens

<400> SEQUENCE: 4

Met Ser Leu Thr Lys Thr Glu Arg Thr Ile Ile Val Ser Met Trp Ala
1               5                   10                  15

Lys Ile Ser Thr Gln Ala Asp Thr Ile Gly Thr Glu Thr Leu Glu Arg
            20                  25                  30

Leu Phe Leu Ser His Pro Gln Thr Lys Thr Tyr Phe Pro His Phe Asp
        35                  40                  45

Leu His Pro Gly Ser Ala Gln Leu Arg Ala His Gly Ser Lys Val Val
    50                  55                  60

Ala Ala Val Gly Asp Ala Val Lys Ser Ile Asp Asp Ile Gly Gly Ala
65                  70                  75                  80

Leu Ser Lys Leu Ser Glu Leu His Ala Tyr Ile Leu Arg Val Asp Pro
                85                  90                  95

Val Asn Phe Lys Leu Leu Ser His Cys Leu Leu Val Thr Leu Ala Ala
            100                 105                 110

Arg Phe Pro Ala Asp Phe Thr Ala Glu Ala His Ala Ala Trp Asp Lys
        115                 120                 125

Phe Leu Ser Val Val Ser Ser Val Leu Thr Glu Lys Tyr Arg
    130                 135                 140

<210> SEQ ID NO 5
<211> LENGTH: 147
<212> TYPE: PRT
<213> ORGANISM: Homo sapiens

<400> SEQUENCE: 5

Met Gly His Phe Thr Glu Glu Asp Lys Ala Thr Ile Thr Ser Leu Trp
1               5                   10                  15

Gly Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
```

```
                    50                   55                    60
Gly Lys Lys Val Leu Thr Ser Leu Gly Asp Ala Thr Lys His Leu Asp
 65                  70                  75                   80

Asp Leu Lys Gly Thr Phe Ala Gln Leu Ser Glu Leu His Cys Asp Lys
                 85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Ala Val Ala Ser Ala Leu Ser Ser
130                 135                 140

Arg Tyr His
145

<210> SEQ ID NO 6
<211> LENGTH: 147
<212> TYPE: PRT
<213> ORGANISM: Homo sapiens

<400> SEQUENCE: 6

Met Gly His Phe Thr Glu Glu Asp Lys Ala Thr Ile Thr Ser Leu Trp
 1               5                   10                  15

Gly Lys Val Asn Val Glu Asp Ala Gly Gly Glu Thr Leu Gly Arg Leu
                20                  25                  30

Leu Val Val Tyr Pro Trp Thr Gln Arg Phe Phe Asp Ser Phe Gly Asn
            35                  40                  45

Leu Ser Ser Ala Ser Ala Ile Met Gly Asn Pro Lys Val Lys Ala His
        50                  55                  60

Gly Lys Lys Val Leu Thr Ser Leu Gly Asp Ala Ile Lys His Leu Asp
 65                  70                  75                  80

Asp Leu Lys Gly Thr Phe Ala Gln Leu Ser Glu Leu His Cys Asp Lys
                 85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Gly Val Ala Ser Ala Leu Ser Ser
130                 135                 140

Arg Tyr His
145

<210> SEQ ID NO 7
<211> LENGTH: 321
<212> TYPE: PRT
<213> ORGANISM: Homo sapiens

<400> SEQUENCE: 7

Met Ala Met Ala Thr Lys Gly Gly Thr Val Lys Ala Ala Ser Gly Phe
 1               5                   10                  15

Asn Ala Met Glu Asp Ala Gln Thr Leu Arg Lys Ala Met Lys Gly Leu
                20                  25                  30

Gly Thr Asp Glu Asp Ala Ile Ile Ser Val Leu Ala Tyr Arg Asn Thr
            35                  40                  45

Ala Gln Arg Gln Glu Ile Arg Thr Ala Tyr Lys Ser Thr Ile Gly Arg
        50                  55                  60

Asp Leu Ile Asp Asp Leu Lys Ser Glu Leu Ser Gly Asn Phe Glu Gln
 65                  70                  75                  80
```

```
Val Ile Val Gly Met Met Thr Pro Thr Val Leu Tyr Asp Val Gln Glu
             85                  90                  95

Leu Arg Arg Ala Met Lys Gly Ala Gly Thr Asp Glu Gly Cys Leu Ile
            100                 105                 110

Glu Ile Leu Ala Ser Arg Thr Pro Glu Glu Ile Arg Arg Ile Ser Gln
            115                 120                 125

Thr Tyr Gln Gln Gln Tyr Gly Arg Ser Leu Glu Asp Asp Ile Arg Ser
130                 135                 140

Asp Thr Ser Phe Met Phe Gln Arg Val Leu Val Ser Leu Ser Ala Gly
145                 150                 155                 160

Gly Arg Asp Glu Gly Asn Tyr Leu Asp Asp Ala Leu Val Arg Gln Asp
                165                 170                 175

Ala Gln Asp Leu Tyr Glu Ala Gly Glu Lys Lys Trp Gly Thr Asp Glu
            180                 185                 190

Val Lys Phe Leu Thr Val Leu Cys Ser Arg Asn Arg Asn His Leu Leu
            195                 200                 205

His Val Phe Asp Glu Tyr Lys Arg Ile Ser Gln Lys Asp Ile Glu Gln
210                 215                 220

Ser Ile Lys Ser Glu Thr Ser Gly Ser Phe Glu Asp Ala Leu Leu Ala
225                 230                 235                 240

Ile Val Lys Cys Met Arg Asn Lys Ser Ala Tyr Phe Ala Glu Lys Leu
                245                 250                 255

Tyr Lys Ser Met Lys Gly Leu Gly Thr Asp Asp Asn Thr Leu Ile Arg
            260                 265                 270

Val Met Val Ser Arg Ala Glu Ile Asp Met Leu Asp Ile Arg Ala His
            275                 280                 285

Phe Lys Arg Leu Tyr Gly Lys Ser Leu Tyr Ser Phe Ile Lys Gly Asp
            290                 295                 300

Thr Ser Gly Asp Tyr Arg Lys Val Leu Leu Val Leu Cys Gly Gly Asp
305                 310                 315                 320

Asp

<210> SEQ ID NO 8
<211> LENGTH: 1753
<212> TYPE: DNA
<213> ORGANISM: Homo sapiens

<400> SEQUENCE: 8 cagcccccgcc cctacctgtg gaagcccagc cgcccgctcc cgcggataaa aggcgcggag      60
tgtccccgag gtcagcgagt gcgcgctcct cctcgcccgc cgctaggtcc atcccggccc     120
agccaccatg tccatccact tcagctcccc ggtattcacc tcgcgctcag ccgccttctc     180
gggccgcggc gcccaggtgc gcctgagctc cgctcgcccc ggcggccttg cagcagcag     240 cctctacggc ctcggcgcct cacggccgcg cgtggccgtg cgctctgcct atggggccc     300 ggtgggcgcc ggcatccgcg aggtcaccat taaccagagc ctgctggccc cgctgcggct     360
ggacgccgac ccctcccctcc agcgggtgcg ccaggaggag agcgagcaga tcaagaccct     420
caacaacaag tttgcctcct tcatcgacaa ggtgcggttt ctggagcagc agaacaagct     480
gctggagacc aagtggacgc tgctgcagga gcagaagtcg gccaagagca gccgcctccc     540
agacatcttt gaggcccaga ttgctggcct tcggggtcag cttgaggcac tgcaggtgga     600 tggggccgc ctggaggcgg agctgcggag catgcaggat gtggtggagg acttcaagaa     660
taagtacgaa gatgaaatta accaccgcac agctgctgag aatgagtttg tggtgctgaa     720
```

-continued

| | |
|---|---|
| gaaggatgtg gatgctgcct acatgagcaa ggtggagctg gaggccaagg tggatgccct | 780 |
| gaatgatgag atcaacttcc tcaggaccct caatgagacg gagttgacag agctgcagtc | 840 |
| ccagatctcc gacacatctg tggtgctgtc catggacaac agtcgctccc tggacctgga | 900 |
| cggcatcatc gctgaggtca aggcgcagta tgaggagatg gccaaatgca gccgggctga | 960 |
| ggctgaagcc tggtaccaga ccaagtttga ccctccag gcccaggctg gaagcatgg | 1020 |
| ggacgacctc cggaataccc ggaatgagat ttcagagatg aaccgggcca tccagaggct | 1080 |
| gcaggctgag atcgacaaca tcaagaacca gcgtgccaag ttggaggccg ccattgccga | 1140 |
| ggctgaggag cgtggggagc tggcgctcaa ggatgctcgt gccaagcagg aggagctgga | 1200 |
| agccgccctg cagcggggca agcaggatat ggcacggcag ctgcgtgagt accaggaact | 1260 |
| catgagcgtg aagctggccc tggacatcga gatcgccacc taccgcaagc tgctggaggg | 1320 |
| cgaggagagc cggttggctg agatggagt gggagccgtg aatatctctg tgatgaattc | 1380 |
| cactggtggc agtagcagtg gcggtggcat tgggctgacc ctcgggggaa ccatgggcag | 1440 |
| caatgccctg agcttctcca gcagtgcggg tcctgggctc ctgaaggctt attccatccg | 1500 |
| gaccgcatcc gccagtcgca ggagtgcccg cgactgagcc gcctcccacc actccactcc | 1560 |
| tccagccacc acccacaatc acaagaagat tcccacccct gcctccatg cctggtccca | 1620 |
| agacagtgag acagtctgga aagtgatgtc agaatagctt ccaataaagc agcctcattc | 1680 |
| tgaggcctga gtgatccacg tgaaaaaaaa aaaaaaaaaa aaaaaaaaaa aaaaaaaaaa | 1740 |
| aaaaaaaaaa aaa | 1753 |

<210> SEQ ID NO 9
<211> LENGTH: 1788
<212> TYPE: DNA
<213> ORGANISM: Homo sapiens

<400> SEQUENCE: 9

| | |
|---|---|
| attcctgaga gctctcctca ccaagaagca gcttctccgc tccttctagg atctccgcct | 60 |
| ggttcggccc gcctgcctcc actcctgcct ctaccatgtc catcagggtg acccagaagt | 120 |
| cctacaaggt gtccacctct ggccccccggg ccttcagcag ccgctcctac acgagtgggc | 180 |
| ccggttcccg catcagctcc tcgagcttct cccgagtggg cagcagcaac tttcgcggtg | 240 |
| gcctgggcgg cggctatggt ggggccagcg gcatgggagg catcaccgca gttacggtca | 300 |
| accagagcct gctgagcccc cttgtcctgg aggtggaccc caacatccag gccgtgcgca | 360 |
| cccaggagaa ggagcagatc aagaccctca caacaagtt tgcctccttc atagacaagg | 420 |
| tacggttcct ggagcagcag aacaagatgc tggagaccaa gtggagcctc ctgcagcagc | 480 |
| agaagacggc tcgaagcaac atggacaaca tgttcgagag ctacatcaac aaccttaggc | 540 |
| ggcagctgga gactctgggc caggagaagc tgaagctgga ggcggagctt ggcaacatgc | 600 |
| aggggctggt ggaggacttc aagaacaagt atgaggatga gatcaataag cgtacagaga | 660 |
| tggagaacga atttgtcctc atcaagaagg atgtggatga agcttacatg aacaaggtag | 720 |
| agctggagtc tcgcctggaa gggctgaccg acgagatcaa cttcctcagg cagctatatg | 780 |
| aagaggagat ccgggagctg cagtcccaga tctcggacac atctgtggtg ctgtccatgg | 840 |
| acaacagccg ctccctggac atggacagca tcattgctga ggtcaaggca cagtacgagg | 900 |
| atattgccaa ccgcagccgg gctgaggctg agagcatgta ccagatcaag tatgaggagc | 960 |
| tgcagagcct ggctgggaag cacggggatg acctgcggcg cacaaagact gagatctctg | 1020 |
| agatgaaccg gaacatcagc cggctccagg ctgagattga gggcctcaaa ggccagaggg | 1080 |

| | |
|---|---|
| cttccctgga ggccgccatt gcagatgccg agcagcgtgg agagctggcc attaaggatg | 1140 |
| ccaacgccaa gttgtccgag ctggaggccg ccctgcagcg ggccaagcag acatggcgc | 1200 |
| ggcagctgcg tgagtaccag gagctgatga acgtcaagct ggccctggac atcgagatcg | 1260 |
| ccacctacag gaagctgctg gagggcgagg agagccggct ggagtctggg atgcagaaca | 1320 |
| tgagtattca tacgaagacc accagcggct atgcaggtgg tctgagctcg gcctatgggg | 1380 |
| gcctcacaag ccccggcctc agctacagcc tgggctccag cttttggctct ggcgcgggct | 1440 |
| ccagctcctt cagccgcacc agctcctcca gggccgtggt tgtgaagaag atcgagacac | 1500 |
| gtgatgggaa gctggtgtct gagtcctctg acgtcctgcc caagtgaaca gctgcggcag | 1560 |
| cccctcccag cctacccctc ctgcgctgcc ccagagcctg gaaggaggc cgctatgcag | 1620 |
| ggtagcactg gaacaggag acccacctga ggctcagccc tagccctcag cccacctggg | 1680 |
| gagtttacta cctggggacc cccttgccc atgcctccag ctacaaaaca attcaattgc | 1740 |
| ttttttttt tggtccaaaa taaaacctca gctagctctg ccaatgtc | 1788 |

```
<210> SEQ ID NO 10
<211> LENGTH: 1490
<212> TYPE: DNA
<213> ORGANISM: Homo sapiens

<400> SEQUENCE: 10
```

| | |
|---|---|
| agatatccgc ccctgacacc attcctccct tcccccctcc accggccgcg ggcataaaag | 60 |
| gcgccaggtg agggcctcgc cgctcctccc gcgaatcgca gcttctgaga ccagggttgc | 120 |
| tccgtccgtg ctccgcctcg ccatgacttc ctacagctat cgccagtcgt cggccacgtc | 180 |
| gtccttcgga ggcctgggcg gcggctccgt gcgttttggg ccggggtcg cctttcgcgc | 240 |
| gcccagcatt cacgggggct ccggcggccg cggcgtatcc gtgtcctccg cccgctttgt | 300 |
| gtcctcgtcc tcctcggggg cctacggcgg cggctacggc ggcgtcctga ccgcgtccga | 360 |
| cgggctgctg gcgggcaacg agaagctaac catgcagaac ctcaacgacc gcctggcctc | 420 |
| ctacctggac aaggtgcgcg ccctggaggc ggccaacggc gagctagagg tgaagatccg | 480 |
| cgactggtac cagaagcagg ggcctgggcc ctcccgcgac tacagccact actacacgac | 540 |
| catccaggac ctgcgggaca gattcttgg tgccaccatt gagaactcca ggattgtcct | 600 |
| gcagatcgac aatgcccgtc tggctgcaga tgacttccga accaagtttg agacggaaca | 660 |
| ggctctgcgc atgagcgtgg aggccgacat caacggcctg cgcagggtgc tggatgagct | 720 |
| gaccctggcc aggaccgacc tggagatgca gatcgaaggc ctgaaggaag agctggccta | 780 |
| cctgaagaag aaccatgagg aggaaatcag tacgctgagg ggccaagtgg aggccaggt | 840 |
| cagtgtggag gtggattccg ctccgggcac cgatctcgcc aagatcctga gtgacatgcg | 900 |
| aagccaatat gaggtcatgg ccgagcagaa ccggaaggat gctgaagcct ggttcaccag | 960 |
| ccggactgaa gaattgaacc gggaggtcgc tggccacacg gagcagctcc agatgagcag | 1020 |
| gtccgaggtt actgacctgc ggcgcaccct tcagggtctt gagattgagc tgcagtcaca | 1080 |
| gctgagcatg aaagctgcct tggaagacac actggcagaa acggaggcgc gctttggagc | 1140 |
| ccagctggcg catatccagg cgctgatcag cggtattgaa gcccagctgg gcgatgtgcg | 1200 |
| agctgatagt gagcggcaga atcaggagta ccagcggctc atggacatca gtcgcggct | 1260 |
| ggagcaggag attgccacct accgcagcct gctcgaggga caggaagatc actacaacaa | 1320 |
| tttgtctgcc tccaaggtcc tctgaggcag caggctctgg ggcttctgct gtcctttgga | 1380 |
| gggtgtcttc tgggtagagg gatgggaagg aagggaccct tacccccggc tcttctcctg | 1440 |

```
acctgccaat aaaaatttat ggtccaaggg aaaaaaaaaa aaaaaaaaaa         1490
```

<210> SEQ ID NO 11
<211> LENGTH: 2158
<212> TYPE: DNA
<213> ORGANISM: Homo sapiens

<400> SEQUENCE: 11

```
gccccaggtg cgcttcccct agagagggat tttccggtct cgtgggcaga ggaacaacca   60
ggaacttggg ctcagtctcc accccacagt ggggcggatc cgtcccggat aagacccgct  120
gtctggccct gagtagggtg tgacctccgc agccgcagag gaggagcgca gcccggcctc  180
gaagaacttc tgcttgggtg gctgaactct gatcttgacc tagagtcatg gccatggcaa  240
ccaaaggagg tactgtcaaa gctgcttcag gattcaatgc catggaagat gcccagaccc  300
tgaggaaggc catgaaaggg ctcggcaccg atgaagacgc cattattagc gtccttgcct  360
accgcaacac cgcccagcgc caggagatca ggacagccta caagagcacc atcggcaggg  420
acttgataga cgacctgaag tcagaactga gtggcaactt cgagcaggtg attgtgggga  480
tgatgacgcc cacggtgctg tatgacgtgc aagagctgcg aagggccatg aagggagccg  540
gcactgatga gggctgccta attgagatcc tggcctcccg gacccctgag gagatccggc  600
gcataagcca aacctaccag cagcaatatg gacggagcct tgaagatgac attcgctctg  660
acacatcgtt catgttccag cgagtgctgg tgtctctgtc agctggtggg agggatgaag  720
gaaattatct ggacgatgct ctcgtgagac aggatgccca ggacctgtat gaggctggag  780
agaagaaatg ggggacagat gaggtgaaat ttctaactgt tctctgttcc cggaaccgaa  840
atcacctgtt gcatgtgttt gatgaataca aaggatatc acagaaggat attgaacaga  900
gtattaaatc tgaaacatct ggtagctttg aagatgctct gctggctata gtaaagtgca  960
tgaggaacaa atctgcatat tttgctgaaa agctctataa atcgatgaag gcttgggca  1020
ccgatgataa caccctcatc agagtgatgg tttctcgagc agaaattgac atgttggata 1080
tccgggcaca cttcaagaga ctctatggaa agtctctgta ctcgttcatc aagggtgaca 1140
catctggaga ctacaggaaa gtactgcttg ttctctgtgg aggagatgat taaaataaaa 1200
atcccagaag gacaggagga ttctcaacac tttgaatttt tttaacttca ttttctaca 1260
ctgctattat cattatctca gaatgcttat ttccaattaa aacgcctaca gctgcctcct 1320
agaatataga ctgtctgtat tattattcac ctataattag tcattatgat gctttaaagc 1380
tgtacttgca tttcaaagct tataagatat aaatggagat tttaaagtag aaataaatat 1440
gtattccatg tttttaaaag attactttct actttgtgtt tcacagacat tgaatatatt 1500
aaattattcc atatttctctt ttcagtgaaa aatttttta atggaagact gttctaaaat 1560
cacttttttc cctaatccaa tttttagagt ggctagtagt ttcttcattt gaaattgtaa 1620
gcatccggtc agtaagaatg cccatccagt ttttctatatt tcatagtcaa agccttgaaa 1680
gcatctacaa atctcttttt ttaggttttg tccatagcat cagttgatcc ttactaagtt 1740
tttcatggga gacttccttc atcacatctt atgttgaaat cactttctgt agtcaaagta 1800
taccaaaacc aatttatctg aactaaattc taaagtatgg ttatacaaac catatacatc 1860
tggttaccaa acataaatgc tgaacattcc atattattat agttaatgtc ttaatccagc 1920
ttgcaagtga atggaaaaaa aaataagctt caaactaggt attctgggaa tgatgtaatg 1980
ctctgaattt agtatgatat aaagaaaact ttttgtgct aaaaatactt tttaaaatca 2040
atttttgttga ttgtagtaat ttctatttgc actgtgcctt tcaactccag aaacattctg 2100
```
aagatgtact tggatttaat taaaaagttc actttgtaag aaaaaaaaaa aaaaaaa        2158

<210> SEQ ID NO 12
<211> LENGTH: 54
<212> TYPE: DNA
<213> ORGANISM: Artificial sequence
<220> FEATURE:
<223> OTHER INFORMATION: mRNA complementary hybridization probe

<400> SEQUENCE: 12
tcatggccct tcgcagctct tgcacgtcat acagcaccgt gggcgtcatc atcc        54

<210> SEQ ID NO 13
<211> LENGTH: 54
<212> TYPE: DNA
<213> ORGANISM: Artificial sequence
<220> FEATURE:
<223> OTHER INFORMATION: mRNA complementary hybridization probe

<400> SEQUENCE: 13
tcagcctcgg caatggcggc ctccaacttg gcacgctggt tcttgatgtt gtcg        54

<210> SEQ ID NO 14
<211> LENGTH: 54
<212> TYPE: DNA
<213> ORGANISM: Artificial sequence
<220> FEATURE:
<223> OTHER INFORMATION: mRNA complementary hybridization probe

<400> SEQUENCE: 14
tggcgttggc atccttaatg gccagctctc cacgctgctc ggcatctgca atgg        54

<210> SEQ ID NO 15
<211> LENGTH: 53
<212> TYPE: DNA
<213> ORGANISM: Artificial sequence
<220> FEATURE:
<223> OTHER INFORMATION: mRNA complementary hybridization probe

<400> SEQUENCE: 15
tggcttcgca tgtcactcag gatcttggcg agatcggtgc ccggagcgga atc        53

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
agtacctcct ttggttgcca        20

<210> SEQ ID NO 17
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 17

-continued cagaggagga gcgcacg                                                      17

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
gggactgcag ctctgtcaac                                                   20

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
ctgcctacat gagcaaggtg                                                   20

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
ctccacttgg tctccagcat                                                   20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
ggagcagatc aagaccctca                                                   20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
gtcgatctgc aggacaatcc                                                   20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
ccgcgactac agccactact                                                   20

<210> SEQ ID NO 24
<211> LENGTH: 22
<212> TYPE: DNA
<213> ORGANISM: Artificial sequence
<220> FEATURE:

-continued

```
<223> OTHER INFORMATION: Degenerate oligonucleotide primer
<220> FEATURE:
<221> NAME/KEY: misc_feature
<222> LOCATION: (11)..(16)
<223> OTHER INFORMATION: n is a, c, g, or t

<400> SEQUENCE: 24
ccgactcgag nnnnnnatgt gg                                         22
```

METHODS FOR DETECTING FETAL CELLS IN THE MATERNAL BLOOD

RELATED APPLICATIONS

This Application is a National Phase of PCT Patent Application No. PCT/IL2008/000598 having International filing date of May 1, 2008, which claims the benefit of U.S. Provisional Patent Application No. 60/924,149 filed on May 1, 2007. The contents of the above Applications are all incorporated herein by reference.

FIELD AND BACKGROUND OF THE INVENTION

The present invention, in some embodiments thereof, relates to methods of identifying trophoblasts in a biological sample such as a maternal blood and, more particularly, but not exclusively, to utilizing same for prenatal diagnosis.

Prenatal diagnosis involves the identification of chromosomal abnormalities and/or genetic diseases in a human fetus. The current practice for detecting chromosomal aberrations such as presence of extra chromosomes [e.g., the most common condition, Trisomy 21 (Down's syndrome); Klinefelter's syndrome (47, XXY); Trisomy 13 (Patau syndrome); Trisomy 18 (Edwards syndrome); 47, XYY; 47, XXX], absence of chromosomes [e.g., Turner's syndrome (45, X)], various translocations and deletions, as well as diagnosis of genetic diseases (e.g., Cystic Fibrosis, Tay-Sachs Disease) involves invasive procedures, mainly chorionic villus sampling (CVS) and/or amniocentesis.

Because of the increased risk of Down's syndrome in pregnancies of advanced maternal age, in most Western World countries, prenatal diagnosis is offered to women over the age of 35 as well as to women who are known carriers of genetic diseases or chromosomal aberrations (e.g., balanced translocations). Thus, the risk of a pregnant female older than 35 years old to give birth to an infant with a detectable chromosomal aberration has been drastically reduced. However, due to the lack of prenatal diagnosis in younger women, about 80% of Down syndrome infants are born to pregnant females under the age of 35.

CVS or amniocentesis are invasive procedures which carry 2-4% or 0.5-1.0%, respectively, of procedure-related risks of miscarriage. In these procedures the sampled fetal cells are either directly tested by FISH/DNA analyses, or expanded in culture and then subjected to karyotype analyses (e.g., by G-banding).

In attempts to develop a less invasive prenatal diagnosis, various studies have identified markers which can detect fetal cells in the cervical canal (transcervical cells).

Transcervical cells can be retrieved using aspiration, cytobrush, cotton wool swabs, endocervical or intrauterine lavage and be subject to analysis using trophoblast-specific antibodies such as FT1.41.1, PLAP, NDOG-1, NDOG-5, mAb 340 and the human leukocyte antigen (HLA-G) antibody.

PCT Publication No. WO2006/018849 discloses methods of prenatal diagnosis performed on transcervical cells using the HLA-G, PLAP, CHL1 and/or NDOG-1 antibodies followed by FISH analyses.

Non-invasive prenatal diagnosis using the maternal blood has been also attempted. Although rare (e.g., one fetal cell per million nucleated maternal blood cells), fetal trophoblasts, leukocytes and nucleated erythrocytes were found in the maternal blood during the first trimester of pregnancy. However, the isolation of trophoblasts and leukocytes from the maternal blood is limited by the availability of fetal-specific antibodies. In addition, studies have shown that at least 50% of the nucleated red blood cells (NRBCs) isolated from the maternal blood are of maternal origin and moreover, certain cell types tend to persist in the maternal circulation and therefore potentially interfere with diagnosis of subsequent pregnancies (Bianchi D 1996, Troeger C, et al., 1999; Guetta et al., 2004).

Trophoblasts present an attractive target cell type for non-invasive prenatal diagnosis since they can be isolated from a maternal blood early in the first trimester, are distinguishable from maternal blood cells due to their unique structure and are absent in normal adult blood.

Trophoblasts have been isolated from maternal blood by several different methods related to surface antigen expression (e.g., HLA-G) and cell size (van Wijk et al., 2001; Vona et al., 2002). In addition, the present inventors have demonstrated the potential of trophoblasts isolated from the maternal blood to proliferate in vitro under suitable conditions (Guetta, et al., 2005). However, since HLA-G is not exclusively expressed in trophoblasts (Kirszenbaum M et. al. 1995) its use for detection of trophpoblasts in the maternal blood is limited.

Cytokeratins 7 and 8 (CK-7 and CK-8) were found to be expressed in placental tissues and cells (Maldonado-Estrada, J., et al., 2004; Yamamoto R, et al., 1990; Tamai Y., et al., 2000). In addition, the expression level of cytokeratin-19 (CK-19) in the serum throughout the third trimester was associated with severe pre-eclampsia (Tempfer C B., et al., 2000).

Additional background art includes Masuda J., et al., 2004; Daya, D. and Sabet, L. 1991; Oudejans C B, et al., 2003.

SUMMARY OF THE INVENTION

According to an aspect of some embodiments of the present invention there is provided a method of identifying a trophoblast, the method comprising: (a) detecting in cells of a biological sample, with the proviso that the biological sample does not comprise a placental tissue, expression of a trophoblast marker selected from the group consisting of an annexin IV, a cytokeratin-7, a cytokeratin-8 and a cytokeratin-19; and (b) classifying cells exhibiting expression of the trophoblast marker as trophoblasts; thereby identifying the trophoblast.

According to an aspect of some embodiments of the present invention there is provided a method of isolating a trophoblast from a biological sample, comprising: (a) identifying the trophoblast in the biological sample according to the method of the invention, and (b) isolating the trophoblast, thereby isolating the trophoblast from the biological sample.

According to an aspect of some embodiments of the present invention there is provided a method of testing a pregnancy in a subject, comprising identifying in a biological sample of the subject a trophoblast according to the method of the invention, wherein a presence of the trophoblast in the biological sample is indicative of the pregnancy in the subject.

According to an aspect of some embodiments of the present invention there is provided a method of prenatally diagnosing a conceptus, comprising (a) identifying in a biological sample of a pregnant female a trophoblast according to the method of the invention, and (b) subjecting the trophoblast to a conceptus diagnostic assay, thereby prenatally diagnosing the conceptus.

According to an aspect of some embodiments of the present invention there is provided a kit for prenatally diagnosing a conceptus, comprising in one container an agent capable of detecting an expression of a trophoblast marker selected from the group consisting of annexin IV, cytokeratin-7, cytokeratin-8 and cytokeratin-19 and in another container a reagent for conceptus diagnosis.

According to an aspect of some embodiments of the present invention there is provided a method of generating a trophoblast culture, comprising (a) isolating trophoblasts according to the method of the invention, and (b) culturing the trophoblasts under conditions suitable for proliferation of the trophoblasts, thereby generating the trophoblast culture.

According to some embodiments of the invention, detecting the expression is effected at an RNA level.

According to some embodiments of the invention, detecting the expression is effected at a protein level.

According to some embodiments of the invention, the method further comprising culturing the trophoblast prior to step (b) under conditions suitable for proliferation of the trophoblast.

According to some embodiments of the invention, the agent capable of detecting the expression of the trophoblast marker comprises an antibody directed against the trophoblast marker.

According to some embodiments of the invention, the agent capable of detecting the expression of the trophoblast marker comprises a polynucleotide probe specifically hybridizable with the trophoblast marker.

According to some embodiments of the invention, the agent capable of detecting the expression comprises a pair of PCR primers for amplification of a complementary DNA (cDNA) molecule of the trophoblast marker.

According to some embodiments of the invention, the biological sample comprises a maternal blood sample.

According to some embodiments of the invention, the biological sample comprises a transcervical sample.

According to some embodiments of the invention, isolating the immunocomplex is effected by magnetic cell sorting (MACS).

According to some embodiments of the invention, isolating the immunocomplex is effected by fluorescence activated cell sorting (FACS).

According to some embodiments of the invention, the conceptus diagnostic assay is effected by a chromosomal analysis.

According to some embodiments of the invention, the chromosomal analysis is effected by fluorescent in situ hybridization (FISH), primed in situ labeling (PRINS), multicolor-banding (MCB) and/or quantitative FISH (Q-FISH).

According to some embodiments of the invention, the conceptus diagnostic assay comprises karyotype analysis.

According to some embodiments of the invention, the karyotype analysis is performed using a staining method selected from the group consisting of G-banding, R-banding, Q-banding and C-banding.

According to some embodiments of the invention, the conceptus diagnostic assay is effected by a DNA analysis.

According to some embodiments of the invention, the DNA analysis comprises comparative genome hybridization (CGH) and/or identification of at least one nucleic acid substitution.

According to some embodiments of the invention, the CGH is effected using metaphase chromosomes and/or a CGH-array.

According to some embodiments of the invention, diagnosing the conceptus comprises identifying at least one chromosomal and/or DNA abnormality, and/or determining a paternity of the conceptus.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is an image depicting two-dimensional gel electrophoresis-based proteomics which compares proteins expressed in placental trophoblasts (violet spots) with those expressed in maternal blood cells (green spots).

Figure 1:
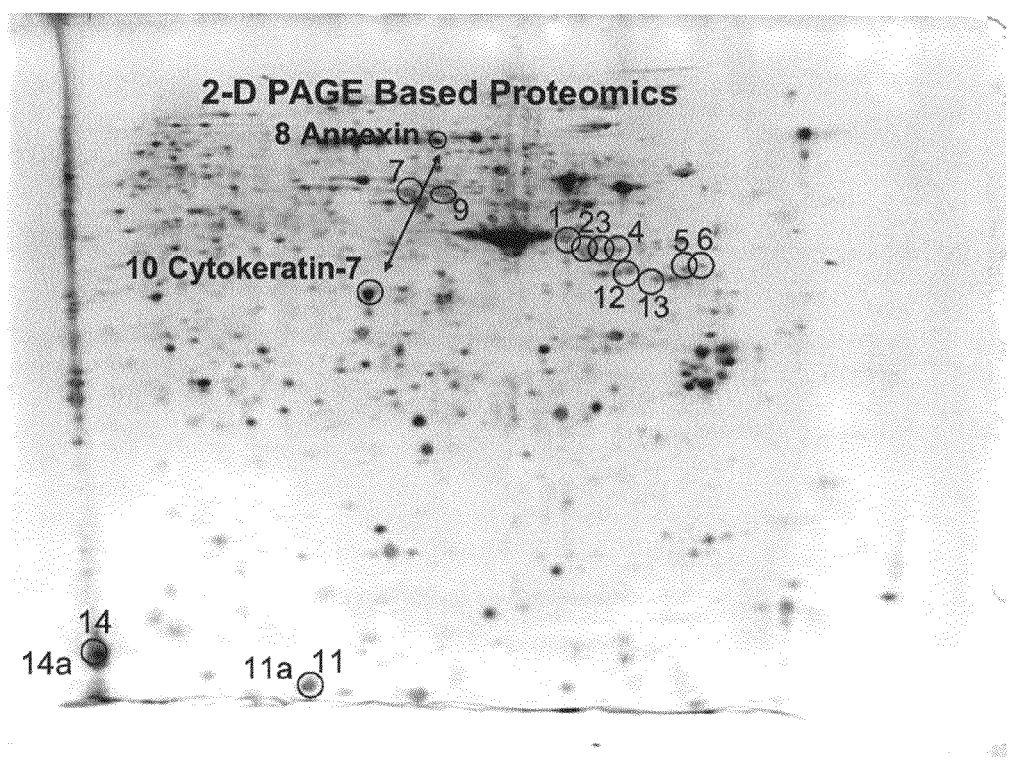
Figure 2A:
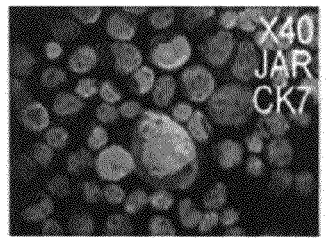
Figure 2B:
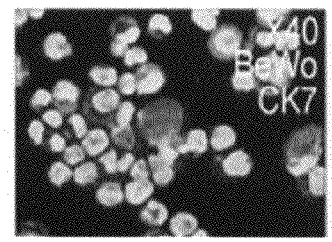
Figure 2C:
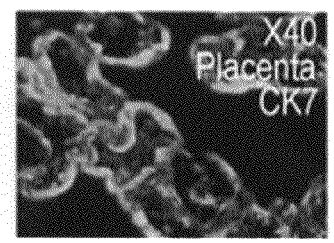
Figure 2D:
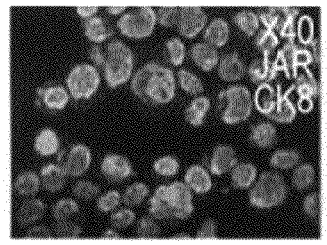
Figure 2E:
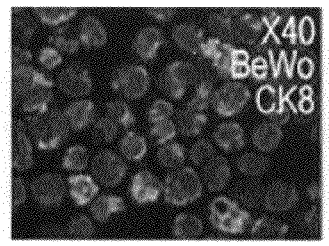
Figure 2F:
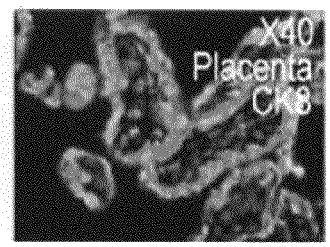
Figure 2G:
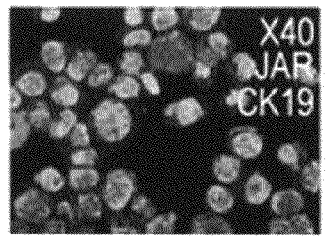
Figure 2H:
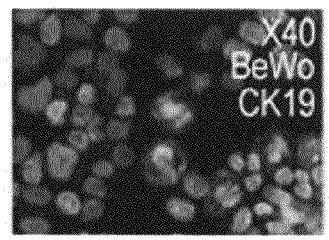
Figure 2I:
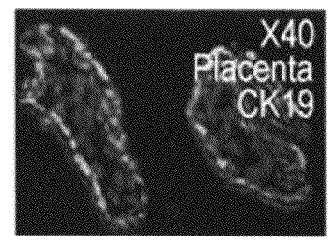
Figure 2J:
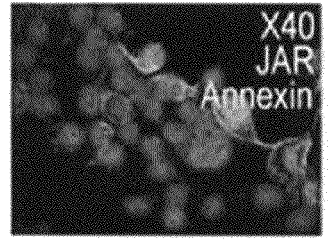
Figure 2K:
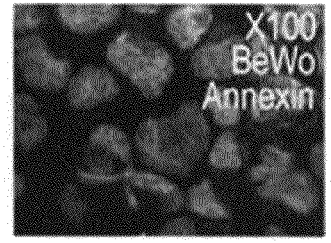
Figure 2L:
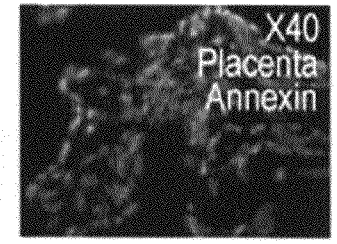

FIGS. 2a-l are images depicting immunofluorescence staining of the trophoblast cell lines JAR (ATCC No. HTB-144; FIGS. 2a, d, g, j) and BeWo (ATCC No. CCL-98; FIGS. 2b, e, h, k) and the placental tissue from a first trimester pregnancy (FIGS. 2c, f, i, l) using monoclonal antibodies directed against the trophoblast markers revealed by the proteomics analysis: CK-7 (cytokeratin-7; FIGS. 2a-c), CK-8 (cytokeratin 8; FIGS. 2d-f), CK-19 (cytokeratin-19; FIGS. 2g-i), and Annexin IV (FIGS. 2j-l). Note that the cytokeratins 7, 8 and 19 were strongly expressed in placental sections as well as in the trophoblast cell lines, whereas Annexin IV was also expressed in all 3 sources, however at lower intensities.

Figure 3:
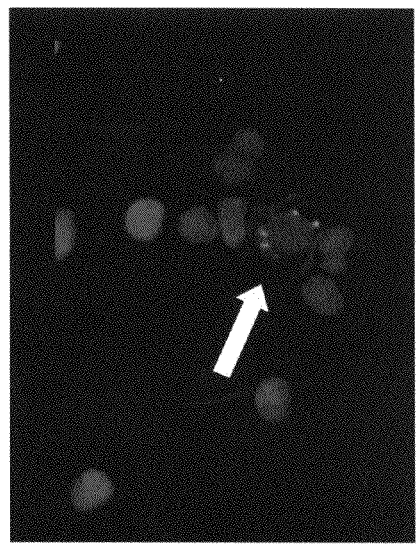

FIG. 3 is an image depicting immunofluorescence staining of maternal peripheral blood cells enriched by magnetic cell sorting (MACS) with the anti-annexin IV antibody (sc-46693, Santa Cruz Biotechnology). The arrow points at an annexin-IV-positive cell of a fetal origin with green fluorescent (FITC) staining.

Figure 4:
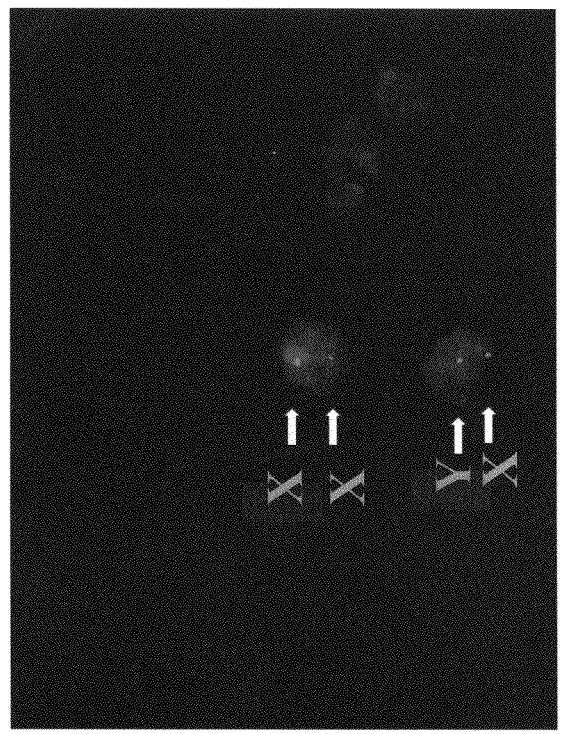

FIG. 4 is an image depicting FISH staining of maternal blood cells enriched by anti-annexin IV-MACS. Note that the upper cell is of a maternal origin as evidenced by the presence of two green hybridization signals corresponding to two X chromosomes and the lower cell is of a fetal origin as it contains one green signal (of the X-chromosome) and one orange signal (of the Y-chromosome).

Figure 5B:
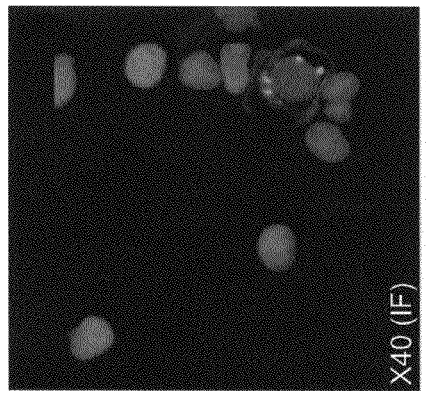
Figure 5D:
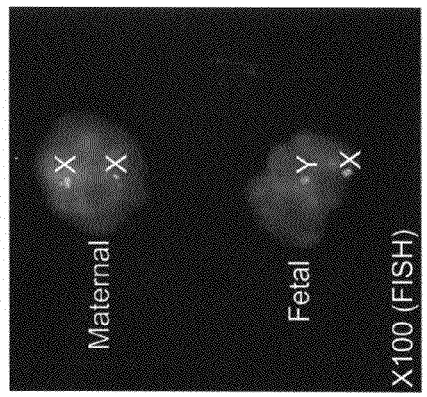
Figure 5A:
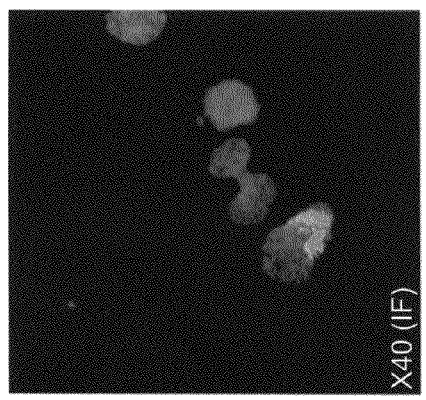
Figure 5C:

FIGS. 5a-d are images depicting immunofluorescence (FIGS. 5a-c) and FISH (FIG. 5d) analyses of maternal peripheral blood cells enriched by magnetic cell sorting with anti-annexin IV antibody. Note the green labelling (Green FITC) resulting from the specific binding of the anti-annexin IV antibody, and the blue labelling (DAPI) of the nuclear counter-staining (FIGS. 5a-c). Also note the specific FISH hybridization signals resulting from the hybridization to the X (green signal) and Y (orange signal) sex-chromosome probes (FIG. 5d), confirming the fetal origin of the cells. Objective magnifications were X 40 (for FIGS. 5a-c) and X 100 (for FIG. 5d).

Figure 6A:
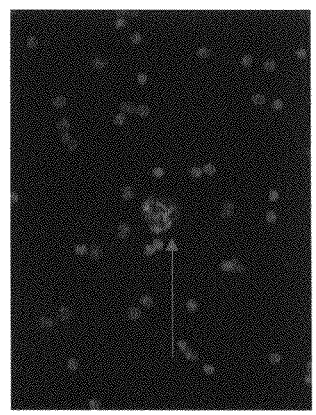
Figure 6B:
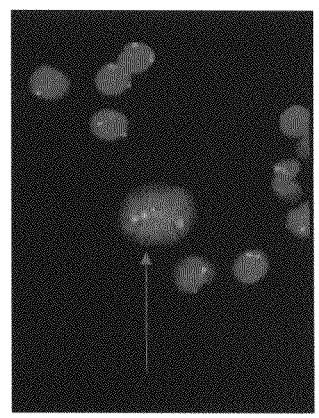

FIGS. 6a-b are images depicting immunofluorescence (FIG. 6a) and FISH (FIG. 6b) analyses of trophoblast cells (JAR trophoblasts) in spiking experiments of maternal blood cells. JAR cells which are positively-stained with the anti-CK7 antibody (FITC, Green, FIG. 6a, arrow) exhibit a polyploid karyotype as evidenced by FISH analyses which revealed the presence of three X chromosomes (three green signals) and one Y chromosome (one orange signal) (FIG. 6b, arrow).

Figure 7A:
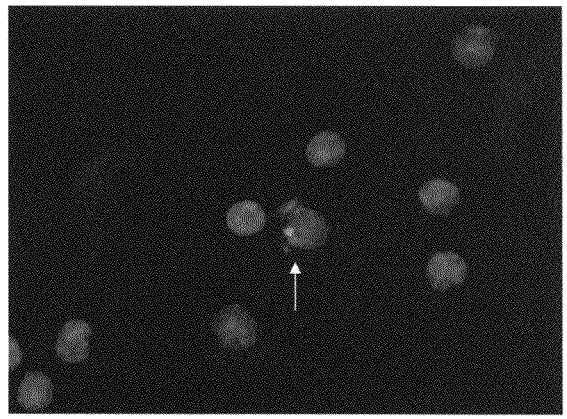
Figure 7B:
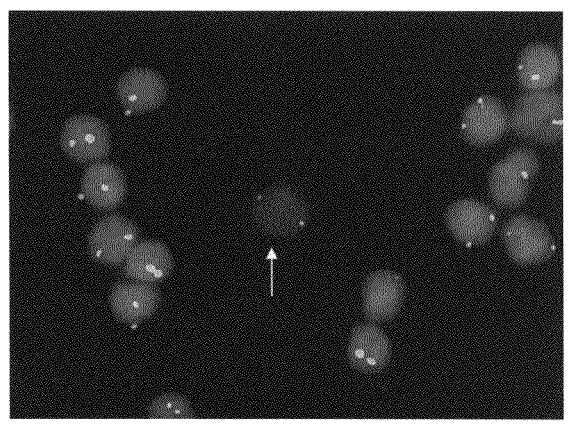

FIGS. 7a-b are images depicting immunofluorescence (FIG. 7a) and FISH (FIG. 7b) analyses of cells of a maternal blood sample processed with a novel MACS protocol developed by the present inventors for use with an intracellular marker (CK7). FIG. 7a-Immunofluorescence staining of a CK7-positive fetal cell (arrow) exhibiting green FITC cytoplasmic staining. Counter nuclear-staining was performed with 4',6-diamidino-2-phenylindole (DAPI). CK-7-negative cells (maternal blood cells) are stained with only blue DAPI nuclear staining. FIG. 7b—FISH analysis confirms the presence of a male cell (of a male fetus, arrow) by the presence of one X-chromosome (green signal) and one Y-chromosome (red signal). The rest of cells (maternal blood cells) exhibit two green signals (XX chromosomes).

FIG. 8 is a histogram depicting the mean number of trophoblasts per a 20 ml blood sample isolated using the annexin IV (n=20) or HLA-G (n=13) based MACS. Note the significant increase (p<0.05) in yield of fetal cells (trophoblasts) using the annexin-IV-based MACS analysis (6.25 trophoblasts per a 20-ml blood sample) as compared to the HLA-G-based MACS (only 1.5 trophoblasts per a 20-ml blood sample).

Figure 9:
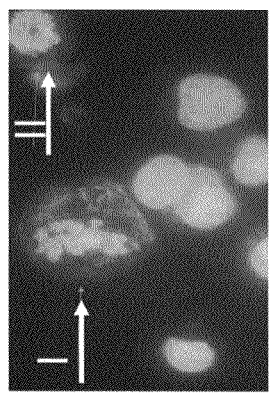

FIG. 9 is an image depicting immunofluorescence of trophoblasts enriched from maternal blood using an anti HLA-G antibody. Shown are 2 trophoblast cells (arrows I and II), positively stained with the HLA-G antibody (green fluorescent cytoplasmic staining) with a chromatin (blue DAPI staining) visibly organized at the metaphase plate. Small surrounding cells are maternal lymphocytes, stained positive with DAPI only.

DESCRIPTION OF SPECIFIC EMBODIMENTS OF THE INVENTION

The present invention, in some embodiments thereof, relates to methods of identifying trophoblasts in a biological sample such as a maternal blood and, more particularly, but not exclusively, to utilizing same for prenatal diagnosis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have uncovered a method of identifying a trophoblast in a biological sample.

Thus, as shown in the Examples section which follows, using comparative proteomics analysis the present inventors have identified proteins which are highly expressed in placental trophoblasts but not in peripheral blood cells (FIGS. 1, 2a-l, Example 1) and which can be used for a non-invasive prenatal diagnosis. These proteins include cytokeratin 7 (GenBank Accession No. NP_005547; SEQ ID NO:1), cytokeratin 8 (GenBank Accession No. NP_002264; SEQ ID NO:2), cytokeratin 19 (GenBank Accession No. NP_002267; SEQ ID NO:3) and annexin IV (GenBank Accession No. NP_001144; SEQ ID NO:7). In addition, as described in Examples 2-4 of the Examples section which follows, the present inventors demonstrated magnetic cell sorting (MACS) enrichment of trophoblasts from maternal peripheral blood samples using antibodies specific to the annexin IV or CK-7 trophoblast markers (FIGS. 3, 4, 5a-d, 6a-b, 7a-b) which was far more efficient than HLA-G-based MACS enrichment (FIG. 8, Example 5). The trophoblasts were further analyzed by FISH staining to detect chromosomal aberrations (FIGS. 4, 5a-d, 6a-b, 7a-b) of the fetus. Moreover, trophoblasts isolated from the maternal blood were shown capable of proliferating in culture (Guetta et al., 2005; FIG. 9 and Example 6 herein below). Thus, these results demonstrate a new method of identifying trophoblasts from a biological sample such as the maternal blood which can be used for prenatal diagnosis either directly or on cultured trophoblasts.

Thus, according to one aspect of the invention, there is provided a method of identifying a trophoblast. The method is effected by detecting in cells of a biological sample expression of a trophoblast marker selected from the group consisting of an annexin IV, a cytokeratin-7, a cytokeratin-8 and a cytokeratin-19; and classifying cells exhibiting expression of the trophoblast marker as trophoblasts; thereby identifying the trophoblast.

As used herein the term "trophoblast" refers to an epithelial cell (whether viable or not) which is derived from the placenta of a mammalian embryo or fetus; a trophoblast typically contacts the uterine wall. There are three types of trophoblast cells in the placental tissue: the villous cytotrophoblast, the syncytiotrophoblast, and the extravillous trophoblast, and as such, the term "trophoblast" as used herein encompasses any of these cells. The villous cytotrophoblast cells are specialized placental epithelial cells which differentiate, proliferate and invade the uterine wall to form the villi. Cytotrophoblasts, which are present in anchoring villi can fuse to form the syncytiotrophoblast layer or form columns of extravillous trophoblasts (Cohen S. et al., 2003. J. Pathol. 200: 47-52).

As used herein the phrase "identifying a trophoblast" refers to identification of a trophoblast cell and/or a trophoblast-containing sample.

The biological sample used by the method of this aspect of the invention can be a blood sample, a transcervical sample, an intrauterine sample or an amniocyte sample derived from a pregnant female at any stage of gestation. A blood sample obtained from a pregnant female is further referred to as a "maternal blood sample" hereinafter. In exemplary embodiments the biological sample is not placenta.

The biological sample may be obtained using invasive or non-invasive methods such as described hereinbelow.

A maternal blood sample can be obtained by drawing blood from a peripheral blood vessel (e.g., a peripheral vein), or from any other blood vessel such as the utertine vein (e.g., as described in Kozma, R., et al., Human Reproduction, 1: 335-336). The blood sample can be of about 20-25 ml. According to some embodiments of the invention, the peripheral blood sample is obtained during the first trimester of pregnancy (e.g., between the 6-13 weeks of gestation).

Once obtained, the blood sample can be subject to a density gradient [such as the Unisep Maxi tubes (Novamed Jerusalem, Israel, U16 tubes)] which separates nucleated cells (the Buffy-coat layer) from the plasma or the un-nucleated red blood cells. According to some embodiments of the invention, from a 20-ml peripheral blood sample about $1-5 \times 10^7$ nucleated cells are obtained.

Transcervical or intrauterine biological samples can be obtained by mucus aspiration (see e.g., Sherlock, J., et al., 1997. J. Med. Genet. 34: 302-305; Miller, D. and Briggs, J.

1996. Early Human Development 47: S99-S102), cytobrush (see e.g., Cioni, R., et al., 2003. Prent. Diagn. 23: 168-171; Fejgin, M. D., et al., 2001. Prenat. Diagn. 21: 619-621), cotton wool swab (see e.g., Griffith-Jones, M. D., et al., 1992. Supra), endocervical lavage (see e.g., Massari, A., et al., 1996. Hum. Genet. 97: 150-155; Griffith-Jones, M. D., et al., 1992. Supra; Schueler, P. A. et al., 2001. 22: 688-701), and intrauterine lavage (see e.g., Cioni, R., et al., 2002. Prent. Diagn. 22: 52-55; Ishai, D., et al., 1995. Prenat. Diagn. 15: 961-965; Chang, S-D., et al., 1997. Prenat. Diagn. 17: 1019-1025; Sherlock, J., et al., 1997, Supra; Bussani, C., et al., 2002. Prenat. Diagn. 22: 1098-1101).

According to some embodiments of the invention, a transcervical biological sample is obtained between the $3^{rd}$ to $15^{th}$ week of gestation.

An amniocyte sample can be obtained by amniocentesis which is usually performed between the $14^{th}$ to the $22^{nd}$ week of gestation by inserting a thin needle through the abdomen into the uterus. For example, a sample of about 20-30 ml amniotic fluid can be removed.

It should be noted that once obtained, the biological sample can be further processed [e.g., subject to centrifugation, labeling, cell lysis, extraction of macromolecules (e.g., polynucleotides and polypeptides)] depending on the subsequent trophoblast detection method as described hereinbelow.

As mentioned, identification of a trophoblast according to this aspect of the invention is performed by detecting the expression of a trophoblast marker selected from the group consisting of an annexin IV, a cytokeratin-7, a cytokeratin-8 and a cytokeratin-19.

As used herein, the phrase "expression of a trophoblast marker" refers to the presence and/or level of the gene product (i.e., RNA or protein) of the trophoblast marker.

As used herein the term "annexin IV" refers to the gene product of the Annexin IV genomic sequence encompassed by nucleotides 69862156-69907095 of GenBank Accession No. NC_000002.10, such as the mRNA sequence set forth by SEQ ID NO:11 (GenBank Accession No. NM_001153.3) and the polypeptide sequence set forth by SEQ ID NO:7 (GenBank Accession No. NP_001144.1; CCDS1894.1).

As used herein the term "cytokeratin-7" refers to the gene product of the cytokeratin-7 genomic sequence encompassed by nucleotides 50913221-50928976 of GenBank Accession No. NC_000012.10, such as the mRNA sequence set forth by SEQ ID NO:8 (GenBank Accession No. NM_005556.3) and the polypeptide sequence set forth by SEQ ID NO:1 (GenBank Accession No. NP_005547.3; CCDS8822.1).

As used herein the term "cytokeratin-8" refers to the gene product of the cytokeratin-8 genomic sequence encompassed by nucleotides 51577238-51585127 of GenBank Accession No. NC_000012.10, such as the mRNA sequence set forth by SEQ ID NO:9 (GenBank Accession No. NM_002273.2) and the polypeptide sequence set forth by SEQ ID NO:2 (GenBank Accession No. NP_002264.1; CCDS8841.1).

As used herein the term "cytokeratin-19" refers to the gene product of the cytokeratin-19 genomic sequence encompassed by nucleotides 36933395-36938167 of GenBank Accession No. NC_000017.9, such as the mRNA sequence set forth by SEQ ID NO:10 (GenBank Accession No. NM_002276.4) and the polypeptide sequence set forth by SEQ ID NO:3 (GenBank Accession No. NP_002267.2; CCDS11399.1).

Detecting the presence and/or level of the RNA trophoblast marker of the invention can be performed using an RNA detection method such as Northern blot analysis [e.g., using a labeled DNA or RNA probe which includes a nucleic acid sequence that is complementary to at least a portion of the nucleic acid sequence of the RNA trophoblast marker (e.g., SEQ ID NOs:8-11) and detecting the bound probe using autoradiography, a colorimetric reaction, or chemiluminescence, depending on the type of label used], RT-PCR analysis [which detects presence of a specific RNA sequence using specific PCR primers], semi-quantitative RT-PCR [which compares the relative expression level of a specific RNA between different samples, by adjusting the number of PCR cycles according to known reference samples], real-time RT-PCR [which enables both detection and quantification (as absolute number of copies or relative amount when normalized to an RNA input) of a specific RNA sequence], RNA in situ hybridization [which enables the detection and localization of specific RNA molecules within a cell], in situ RT-PCR stain [which is performed on fixed cells using an apparatus such as the laser-capture microdissection PixCell II™ Laser Capture Microdissection (LCM) system available from Arcturus Engineering (Mountainview, Calif., USA), or PALM, Germany] as described in Nuovo, G. J. et al. (1993) Am J Surg Pathol 17, 683-690; and Komminoth, P. et al. (1994) Pathol Res Pract 190, 1017-1025)] and oligonucleotide microarray [e.g., using oligonucleotide probes (e.g., 20-25 nucleic acids in length, capable of specifically hybridizing to the RNA-of-interest) which are attached to a solid surface (e.g., a glass wafer) such as the Affymetrix® GeneChip® Microarray (Affymetrix, Inc., Santa Clara, Calif., USA)].

Non-limiting examples of complementary DNA probes (which are in the antisense direction with respect to the mRNA sense sequence) which can be used for the detection of annexin IV, cytokeratin-7, cytokeratin-8 or cytokeratin-19 RNA by Northern Blot or RNA in situ hybridization are provided in SEQ ID NOs:12, 13, 14 or 15, respectively. Guidelines and tools for designing probes for RNA in situ hybridization or Northern blot hybridization are described in Brain Research Protocols, 4: 82-91, 1999; and in Hyper Text Transfer Protocol://World Wide Web (dot) anst (dot) uu (dot) se/vigie517/ishprobe (dot) htm.

Suitable polynucleotide probes are specifically hybridizable with their target mRNA sequences (e.g., hybridize to the trophoblast marker RNA but not to other RNA sequences in the sample). By way of example, hybridization of short polynucleotide probes (below 200 nucleotides in length) can be effected by the following hybridization protocols depending on the desired stringency; (i) an hybridization solution of 6×SSC and 1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACI, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACI, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C. Variations in the hybridization conditions (e.g., hybridization solution, wash solutions and temperatures) can be made by one skilled in the art according to the probe length and its G/C content. For example, for polynucleotide probes larger than 200 nucleotides, the hybridization/washes temperatures can be about 55-80° C. (e.g., 65° C.) and the hybridization/wash solutions can include formamide (e.g., 50%).

Non-limiting examples of RT-PCR primer pairs which can be used for the detection of annexin IV, cytokeratin-7, cytokeratin-8 or cytokeratin-19 RNA by RT-PCR are provided in SEQ ID NOs:16-17, 18-19, 20-21 or 22-23, respectively.

Detecting the presence and/or level of the protein trophoblast marker of the invention can be performed using a protein detection method such as using antibodies specific to the protein trophoblast marker (e.g., SEQ ID NOs:1, 2, 3 or 7, see for example, the antibodies described in the Examples section which follows) in Western blot analysis, Enzyme-linked immunosorbent assay (ELISA), Fluorescence-activated cell sorting (FACS) or radio-immuno assay (RIA), or in situ by immunohistochemistry, immunofluorescence or activity staining which can be followed by counterstaining of cell nuclei, using, for example, Hematoxylin, Giemsa, or DAPI stain.

The term "antibody" as used in this invention includes intact molecules as well as functional fragments thereof, such as Fab, F(ab')2, Fv or single domain molecules such as VH and VL to an epitope of an antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference); Goldenberg, U.S. Pat. Nos. 4,036,945 and 4,331,647, and references contained therein, which patents are hereby incorporated by reference in their entirety; Porter, R. R. [Biochem. J. 73: 119-126 (1959)]; Inbar et al. [Proc. Nat'l Acad. Sci. USA 69:2659-62 (19720]; Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety; Larrick and Fry [Methods, 2: 106-10 (1991)].

Another form of antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, J. W. and Fry, K. E. (1991). PCR Amplification of Antibody Genes. METHODS: A Companion to Methods in Enzymology 2(2), 106-110.

The antibody used by the method of the invention can be directly conjugated to a label [e.g., a fluorescent label such as fluorescein (FITC), Texas Red, rhodamine, or a radioactive isotope, e.g., $^{131}$I], a member of an affinity pair (e.g., biotin or digoxigenin (DIG) which can bind streptavidin or a DIG antibody, respectively) or an enzyme (e.g., alkaline phosphatase, peroxidase).

Non-limiting examples of antibodies which can be used to detect the protein trophoblast marker of the invention include anti-annexin IV antibodies [e.g., mouse anti-annexin IV clone D2 (sc-46693, Santa cruz Biotechnology)], anti-cytokeratin-7 antibodies [e.g., mouse anti-human cytokeratin-7 clone OV-TL12/30 (M701801, Dako); mouse IgG1 anti Cytokeratin 7 (Santa cruze, e.g., sc-70934, sc-70933, sc-70935, sc-51585, sc-65214, sc-53263, sc-52322, sc-23876; GeneTex, inc GTX72603, GTX23973, GTX17138, GTX40206, GTX17069, GTX29021, GTX23973, GTX23973; NOVUS NB-100-2777, NOVUS NB500-322), mouse IgG2b anti-Cytokeratin 7 (Santa cruze e.g., sc-53264)], anti-cytokeratin-8 antibodies [e.g., mouse anti-human cytokeratin 8 clone LP3K (0200-0618, Serotec); mouse IgG2a anti-Cytokeratin 8 (Santa cruze sc-58736), mouse IgG1 anti-Cytokeratin 8 (Santa cruze sc-70937, sc-58740, sc-8020; GeneTex, inc GTX22530, GTX22531, GTX40207, GTX29023; NOVUS NB100, Southern Biotech 10080-01), mouse IgG2a anti-Cytokeratin 8 (Santa cruze sc-73480), mouse IgM anti-Cytokeratin 8 (Santa cruze sc-58737; GeneTex, inc GTX27506, GTX20758)] and anti-cytokeratin-19 antibodies [e.g., clone RCK 108 (M0888, Dako); mouse IgG1 anti-Cytokeratin 19 (Santa cruze sc-6278, sc-51584, sc-53257, sc-53258, sc-53003; NOVUS NB-500-358, NB100-2781), IgG2a anti-Cytokeratin 19 (GeneTex, inc. GTX73588, GTX27754, GTX28804; BioLegend 628501/2, SEROTEC 5552-9009, Southern Biotech 10090-01), IgG1 anti-Cytokeratin 19 (GeneTex, inc. GTX73697, GTX27755, GTX40210, GTX29221)].

As mentioned above, the biological sample is processed according to the method utilized for identifying trophoblasts. For example, for in situ detection of the trophoblast marker using a protein (e.g., immunocytochemistry, immunofluorescence) or RNA (e.g., in situ RT-PCR, RNA in situ hybridization) detection methods, nucleated cells of the biological sample can be placed on a microscopic slide using for example, a cytocentrifuge [e.g., Cytofunnel Chamber Cytocentrifuge (Thermo-Shandon, England)]. It should be noted that the conditions used for cytocentrifugation depend on the murkiness of the biological sample; if the specimen contains only a few cells, the cells are first centrifuged for 5 minutes and then suspended with a small volume (e.g., 1 ml) of fresh medium or PBS. Once prepared, the cytospin slides can be kept in 95% alcohol until further use.

For RNA detection methods such as Northern blot, RT-PCR, oligonucleotide microarray, or protein detection methods such as Western blot, RIA or ELISA, the nucleated cells of the biological sample are subjected to cell lysis followed by extraction of the RNA or protein molecules.

For FACS analysis, the nucleated cells of the biological sample are labeled with the appropriate antibodies and loaded on a FACS machine. It should be noted that when antibodies directed against internal antigens (e.g., intracellular proteins such as cytokeratin-7, 8 or 19) are employed, the nucleated cells of the biological sample can be first permeabilized using e.g., a solution including saponin.

The classification of trophoblasts or trophoblast-containing samples can be qualitative and/or quantitative and can be performed manually or automatically using e.g., an image analysis apparatus/software. For example, the position of a certain cell (which is classified as a trophoblast) in a specimen can be marked using known methods, such as by marking the microscopic slide itself (e.g., on the back surface which does not contain cells), or using cell coordinates as determined using a microscope and/or an image analysis apparatus. Non-limiting examples of image analysis apparatuses include the BioView Duet™ image analysis apparatus (Bio View Ltd. Rehovot, Israel) and the Applied Imaging System (Newcastle England).

The present invention envisages the use of the identified trophoblast markers (i.e., an annexin IV, a cytokeratin-7, a cytokeratin-8 and/or a cytokeratin-19) for determining a pregnancy in a subject.

Thus, according to an aspect of some embodiments of the invention, there is provided a method of testing a pregnancy in a subject. The method is effected by identifying in a biological sample of the subject a trophoblast according to the teachings described above, wherein a presence of the trophoblast in the biological sample is indicative of the pregnancy in the subject.

The biological sample used according to this aspect of the invention can be a blood sample, a transcervical sample or an intrauterine sample.

According to some embodiments of the invention, an expression level of the trophoblast marker above a predetermined threshold is indicative of the pregnancy in the subject. The predetermined threshold can be determined according to reference samples obtained from non-pregnant control subjects.

Once identified, the trophoblast can be further isolated from the biological sample.

Thus, according to another aspect of the invention there is provided a method of isolating a trophoblast from a biological sample. The method is effected by identifying the trophoblast in the biological sample according to the teachings described above and isolating the trophoblast, thereby isolating the trophoblast from the biological sample.

As used herein the phrase "isolating a trophoblast" refers the physical isolation of a trophoblast cell from a heterogeneous population of cells (e.g., the other cells within the trophoblast-containing biological sample).

Physical isolation of a trophoblast cell can be performed using methods which involve immunocomplex formation between the trophoblast cell and an antibody (or antibodies; e.g., a combination of anti-annexin IV and anti-cytokeratin-7) specifically bindable to an antigen(s) expressed on or in the cell. Alternatively, physical isolation of a trophoblast cell can be performed by dissecting the identified trophoblast from a specimen containing same (e.g., using laser capture microdissection).

According to some embodiments of the invention, isolating the trophoblast is performed by contacting the trophoblast-containing biological sample (identified as described hereinabove) with an antibody directed against a protein selected from the group consisting of an annexin IV, a cytokeratin-7, a cytokeratin-8 and a cytokeratin-19 under conditions which allow immunocomplex formation between the antibody and the trophoblast, and isolating the immunocomplex from the biological sample.

The cells of the trophoblast-containing biological sample which form the immunocomplex with the antibody can be cultured (as further described below) or non-cultured cells. In some embodiments contacting of the antibody is effected under conditions which maintain the cells' viable such as to allow expansion of same.

The conditions which are sufficient for the formation of an immunocomplex (e.g., appropriate concentrations, buffers, temperatures, reaction times) as well as methods of optimizing same are known to those skilled in the art, and examples are disclosed herein.

According to some embodiments of the invention, the immunocomplex is formed between an antibody and a cell surface antigen such as annexin IV.

According to some embodiments of the invention, the immunocomplex is formed between an antibody and an intracellular antigen (e.g., cytokeratin-7, 8 or 19).

According to some embodiments of the invention, the immunocomplex is formed between two or more antibodies directed against intracellular and/or cell surface antigens.

The immunocomplex described hereinabove can be isolated from the biological sample using known methods such as fluorescence activated cell sorting (FACS) analysis or magnetic cell sorter (MACS).

For isolation by FACS, cells are labeled with the anti-trophoblast antibody which can be fluorescently labeled (e.g., by FITC) to form a labeled immunocomplex and detection is by means of a cell sorting machine which reads the wavelength of light emitted from each cell as it passes through a light beam. This method may employ two or more antibodies simultaneously. As mentioned, if the trophoblast marker is an internal marker, the cells can be permeabilized and the FACS analysis can be performed with antibodies or fragments thereof which may easily penetrate the cell and may easily be washed out of the cell following detection. The FACS process may be repeated a number of times using the same or different markers depending on the degree of enrichment required.

For MACS isolation, the immunocomplex can be contacted with immuno-beads, i.e., magnetic beads coupled to an antibody capable of binding directly or indirectly to the immunocomplex formed between the trophoblast and the anti-trophoblast marker antibody. The immuno-beads can be magnetic beads (such as those available from Miltenyi Biotec Bergisch Gladbach, Germany; 130-048-402) coupled with a secondary antibody (which specifically binds the primary antibody), or magnetic beads coupled to a tertiary antibody which binds the secondary antibody such as an anti-FITC-coupled magnetic beads (e.g., Miltenyi Biotec, 130-048-701). Following the addition of the immuno-beads to the trophoblast-containing biological sample, a magnetic field is employed (e.g., using the Mini-Macs© columns available from Miltenyi Biotec, 130-042-201) resulting in the isolation of immuno-positive cells along with the immuno-beads. The immuno-beads are further subject to extensive washes in order to minimize non-trophoblast contamination. The immunocomplex can be separated from the immuno-beads using e.g., low-ionic-strength buffer (Scouten W H and Konecny P. Anal Biochem. 1992, 205: 313-8)]. Following isolation, the immunocomplex can be further subject to an immunological staining using one or more antibodies directed against the trophoblast marker(s) described above.

As mentioned, physical isolation of a trophoblast cell can be performed by laser capture microdissection.

Laser-capture microdissection of cells is used to selectively isolate a specific cell type from a heterogeneous cell population contained on a slide. Methods of using laser-capture microdissection are known in the art (see for example, U.S. Pat. Appl. No. 20030227611 to Fein, Howard et al.; Micke P, et al., 2004. J. Pathol., 202: 130-8; Evans E A, et al., 2003. Reprod. Biol. Endocrinol. 1: 54; Bauer M, et al. 2002.

Paternity testing after pregnancy termination using laser microdissection of chorionic villi. Int. J. Legal Med. 116: 39-42; Fend, F. and Raffeld, M. 2000, J. Clin. Pathol. 53: 666-72).

For example, a trophoblast-containing cell sample (e.g., a cytospin slide of maternal peripheral blood cells) is contacted with a selectively activated surface [e.g., a thermoplastic membrane such as a polyethylene membrane (PEN slides; C. Zeiss, Thornwood, N.Y.)] capable of adhering to a specific cell upon laser activation. The cell sample is subjected to a differential staining which identifies the trophoblast within the cell sample [e.g., a protein detection method such as an immunological staining, e.g., immunocytochemistry or immunofluorescence (using for example, an anti annexin IV, cytokertain-7, 8 and/or 19 antibody) or an RNA detection method such as RNA in situ hybridization, in situ RT-PCR (with a probe or PCR primers specific to the RNA of annexin IV, cytokertain-7, 8 and/or 19)], following which, the cell sample is viewed using a microscope to identify the differentially stained trophoblast cell (i.e., an annexin IV, cytokertain-7, -8 and/or -19-positive cell) and a laser beam routed through an optic fiber [e.g., using the PALM Microbeam system (PALM Microlaser Technologies AG, Bernreid, Germany)] activates the surface which adheres to the selected trophoblast cell. The laser beam uses the ultraviolet (UV, e.g., 337 nm), the far-UV (200-315 nm) and the near-UV (315-400 nm) ray regions which are suitable for the further isolation of DNA, RNA or proteins from the microdissected cell. Following dissection (i.e., the cutting off of the cell), the laser beam blows off the cut cell into a recovery cap of a microtube, essentially as illustrated in Tachikawa T and Irie T, 2004, Med. Electron Microsc., 37: 82-88. It should be noted that for subsequent DNA analysis, the DNA can be extracted using e.g., the alkaline lysis or the proteinase K protocols which are described in Rook M, et al., 2004, Am. J. of Pathology, 164: 23-33.

The present teachings also allow prenatal diagnosis of a conceptus.

As used herein the term "conceptus" refers to an embryo, a fetus or an extraembryonic membrane of an ongoing pregnancy.

The method of prenatally diagnosing a conceptus is effected by identifying in a biological sample of a pregnant female a trophoblast according to the teachings described hereinabove, and subjecting the trophoblast to a conceptus diagnostic assay.

A conceptus diagnostic assay can be performed directly on the trophoblast (whether isolated from the trophoblast-containing sample or not), or can be performed on cultured trophoblast cells.

The conceptus diagnostic assay can be effected by a chromosomal analysis [i.e., an analysis performed on intact chromosomes (in situ, within the cell) in order to determine abnormalities on a chromosome level] and/or by DNA analysis [i.e., an analysis performed on DNA molecules of a cell(s), usually on isolated DNA molecules derived from a cell(s) in order to determine the nucleic acid sequence of the DNA and/or identify changes in DNA sequences (as compared to normal controls) which can be related to diseases or genetic polymorphisms].

According to some embodiments of the invention, the chromosomal analysis is effected by fluorescent in situ hybridization (FISH), primed in situ labeling (PRINS), multicolor-banding (MCB) and/or quantitative FISH (Q-FISH).

Methods of employing FISH analysis on interphase chromosomes are known in the art. Various commercially available probes can be used for the detection of numeric aberrations, translocations, inversion, duplications and deletions in chromosomes. The probes are mixed with an hybridization buffer (e.g., LSI/WCP, Abbott) and a carrier DNA (e.g., human Cot 1 DNA, available from Abbott), applied on microscopic slides containing cytospin specimens of a trophoblast-containing sample, denatured and incubated for hybridization at about 37° C. for 4-60 hours (e.g., 24-48 hours). Following hybridization, the excess of probe is washed off, the cells are counterstained [e.g., using DAPI II counterstain (Abbott)] and the slides are allowed to dry in the dark. Detection of FISH results is performed using a fluorescent microscope, optionally connected to an image analysis apparatus (e.g., an automated scanning device). Similarly, FISH can be employed on metaphase chromosomes.

Non-limiting examples of FISH probes which can be used with the method of the invention include: the CEP X green and Y orange (Abbott cat no. 5J10-51) probes, Vysis® 1p36 Microdeletion Region Probe—LSI p58 (1p36) (SO)/TelVysion™ 1p (SG)/LSI 1q25 (SA); Cri-du-Chat Region Probe—LSI D5S23, D5S721 SpectrumGreen™; Cri-du-Chat Region Probe—LSI EGR1 SpectrumOrange/LSI D5S23, D5S721 SpectrumGreen™; DiGeorge Region Probe—LSI N25 SpectrumOrange/ARSA SpectrumGreen; DiGeorge Region Probe—LSI TUPLE 1 SpectrumOrange/LSI ARSA SpectrumGreen; DiGeorge Region Probe—LSI TUPLE1 (HIRA) SpectrumOrange/TelVysion 22q SpectrumGreen Probe; Kallman Region Probe—LSI KAL SpectrumOrange/CEP® X SpectrumGreen; Miller-Dieker Region/Isolated Lissencephaly Probe LSI LIS1 SpectrumOrange/LSI RARA SpectrumGreen; Prader-Willi/Angelman Region Probe—LSI D15S10 SpectrumOrange/CEP 15 (D15Z1) SpectrumGreen/PML SpectrumOrange™; Prader-Willi/Angelman Region Probe—LSI D15S11 SpectrumOrange/CEP 15 (D15Z1) SpectrumGreen; Prader-Willi/Angelman Region Probe—LSI GABRB3 SpectrumOrange/CEP 15 (D15Z1) SpectrumGreen; Prader-Willi/Angelman Region Probe—LSI SNRPN(SO)/CEP 15 (D15Z1) (SO)/LSI PML (SO); Smith-Magenis Region Probe—LSI SMS Region SpectrumOrange/LSI RARA SpectrumGreen; Sotos Region Probe—LSI NSD1 (5q35) SpectrumOrange™ Probe; SRY Probe LSI SRY Spectrum Orange/CEP X Spectrum Green; SRY Probe—LSI SRY Spectrum Orange; Steroid Sulfatase Deficiency Probe—LSI STS SpectrumOrange/LSI CEP X SpectrumGreen; Williams Region Probe—LSI ELN SpectrumOrange/LSI D7S486, D7S522 SpectrumGreen; Wolf-Hirschhorn Region Probe—LSI WHS SpectrumOrange/CEP 4 SpectrumGreen; Vysis LSI 13 (RB1) 13q14 SpectrumOrange™; Vysis LSI 13 (13q14) SpectrumGreen 32-192018, 05J14-018; Vysis LSI 21 SpectrumOrange 32-190002, 05J13-002; Vysis LSI 22 (BCR) SpectrumGreen 32-192024, 05J17-024; 5-color FISH in a single cell: Vysis MultiVysion PB Multi-color Probe, 32-131085, 05J31-085; Vysis MultiVysion PGT Multi-color Probe, 32-131080, 05J32-080; Vysis ToTelVysion 33-270000, 05J05-001; Telomere probes such as Vysis ToTelVysion 33-270000, 05J05-001 and Telvysion probes; 5-probe FISH for aneuploidy analysis of chromosomes 13, 18, 21, X, Y (can be performed on interphase or metaphase chromosomes); multi-color FISH such as using the Spectral karyotyping SKY probes (Applied Spectral Imaging, Migdal Haemek; Cat. No. SKY000029 SkyPaint™ DNA kit H-5 for Human chromosomes) can be performed on metaphase chromosomes; Chromosome enumeration probes (CEP) for each of the human chromosomes (1-22, X, Y), especially 13, 18, 21, X and Y.

PRINS analysis has been employed in the detection of gene deletion (Tharapel S A and Kadandale J S, 2002. Am. J. Med. Genet. 107: 123-126), determination of fetal sex (Orsetti, B., et al., 1998. Prenat. Diagn. 18: 1014-1022), and identification of chromosomal aneuploidy (Mennicke, K. et al., 2003. Fetal Diagn. Ther. 18: 114-121).

Methods of performing PRINS analysis are known in the art and include for example, those described in Coullin, P. et al. (Am. J. Med. Genet. 2002, 107: 127-135); Findlay, I., et al. (J. Assist. Reprod. Genet. 1998, 15: 258-265); Musio, A., et al. (Genome 1998, 41: 739-741); Mennicke, K., et al. (Fetal Diagn. Ther. 2003, 18: 114-121); Orsetti, B., et al. (Prenat. Diagn. 1998, 18: 1014-1022). Briefly, slides containing interphase chromosomes are denatured for 2 minutes at 71° C. in a solution of 70% formamide in 2×SSC (pH 7.2), dehydrated in an ethanol series (70, 80, 90 and 100%) and are placed on a flat plate block of a programmable temperature cycler (such as the PTC-200 thermal cycler adapted for glass slides which is available from MJ Research, Waltham, Mass., USA). The PRINS reaction is usually performed in the presence of unlabeled primers and a mixture of dNTPs with a labeled dUTP (e.g., fluorescein-12-dUTP or digoxigenin-11-dUTP for a direct or indirect detection, respectively). Alternatively, or additionally, the sequence-specific primers can be labeled at the 5' end using e.g., 1-3 fluorescein or cyanine 3 (Cy3) molecules. Thus, a typical PRINS reaction mixture includes sequence-specific primers (50-200 pmol in a 50 µl reaction volume), unlabeled dNTPs (0.1 mM of dATP, dCTP, dGTP and 0.002 mM of dTTP), labeled dUTP (0.025 mM) and Taq DNA polymerase (2 units) with the appropriate reaction buffer. Once the slide reaches the desired annealing temperature the reaction mixture is applied on the slide and the slide is covered using a cover slip. Annealing of the sequence-specific primers is allowed to occur for 15 minutes, following which the primed chains are elongated at 72° C. for another 15 minutes. Following elongation, the slides are washed three times at room temperature in a solution of 4×SSC/0.5% Tween-20 (4 minutes each), followed by a 4-minute wash at PBS. Slides are then subjected to nuclei counterstain using DAPI or propidium iodide. The fluorescently stained slides can be viewed using a fluorescent microscope and the appropriate combination of filters (e.g., DAPI, FITC, TRITC, FITC-rhodamin).

It will be appreciated that several primers which are specific for several targets can be used on the same PRINS run using different 5' conjugates. Thus, the PRINS analysis can be used as a multicolor assay for the determination of the presence, and/or location of several genes or chromosomal loci.

In addition, as described in Coullin et al., (2002, Supra) the PRINS analysis can be performed on the same slide as the FISH analysis, preferably, prior to FISH analysis.

High-resolution multicolor banding (MCB) on interphase chromosomes is described in details by Lemke et al. (Am. J. Hum. Genet. 71: 1051-1059, 2002). The method uses YAC/BAC and region-specific microdissection DNA libraries as DNA probes for interphase chromosomes. Briefly, for each region-specific DNA library 8-10 chromosome fragments are excised using microdissection and the DNA is amplified using a degenerate oligonucleotide PCR reaction. For example, for MCB staining of chromosome 5, seven overlapping microdissection DNA libraries were constructed, two within the p arm and five within the q arm (Chudoba I., et al., 1999; Cytogenet. Cell Genet. 84: 156-160). Each of the DNA libraries is labeled with a unique combination of fluorochromes and hybridization and post-hybridization washes are carried out using standard protocols (see for example, Senger et al., 1993; Cytogenet. Cell Genet. 64: 49-53). Analysis of the multicolor-banding can be performed using the isis/mFISH imaging system (MetaSystems GmbH, Altlussheim, Germany). It will be appreciated that although MCB staining on interphase chromosomes was documented for a single chromosome at a time, it is conceivable that additional probes and unique combinations of fluorochromes can be used for MCB staining of two or more chromosomes at a single MCB analysis. Thus, this technique can be used along with the present invention to identify fetal chromosomal aberrations, particularly, for the detection of specific chromosomal abnormalities which are known to be present in other family members.

Quantitative FISH (Q-FISH) enables the detection of chromosomal abnormalities by measuring variations in fluorescence intensity of specific probes. Q-FISH can be performed using Peptide Nucleic Acid (PNA) oligonucleotide probes. PNA probes are synthetic DNA mimics in which the sugar phosphate backbone is replaced by repeating N-(2-aminoethyl) glycine units linked by an amine bond and to which the nucleobases are fixed (Pellestor F and Paulasova P, 2004; Chromosoma 112: 375-380). Thus, the hydrophobic and neutral backbone enables high affinity and specific hybridization of the PNA probes to their nucleic acid counterparts (e.g., chromosomal DNA). Such probes have been applied on interphase nuclei to monitor telomere stability (Slijepcevic, P. 1998; Mutat. Res. 404:215-220; Henderson S., et al., 1996; J. Cell Biol. 134: 1-12), the presence of Fanconi anemia (Hanson H, et al., 2001, Cytogenet. Cell Genet. 93: 203-6) and numerical chromosome abnormalities such as trisomy 18 (Chen C, et al., 2000, Mamm. Genome 10: 13-18), as well as monosomy, duplication, and deletion (Taneja K L, et al., 2001, Genes Chromosomes Cancer. 30: 57-63).

Alternatively, Q-FISH can be performed by co-hybridizing whole chromosome painting probes (e.g., for chromosomes 21 and 22) on interphase nuclei as described in Truong K et al, 2003, Prenat. Diagn. 23: 146-51.

Any of the chromosomal analysis methods described hereinabove which are performed on a trophoblast cell of the maternal biological sample can be used for detecting chromosomal abnormalities in the conceptus.

As used herein, the phrase "chromosomal abnormality" refers to an abnormal number of chromosomes (e.g., trisomy 21, monosomy X) or to chromosomal structure abnormalities (e.g., deletions, translocations, inversion, etc).

According to some embodiments of the invention, the chromosomal abnormality can be chromosomal aneuploidy (i.e., complete and/or partial trisomy and/or monosomy), translocation, subtelomeric rearrangement, deletion, microdeletion, inversion and/or duplication (i.e., complete an/or partial chromosome duplication).

According to some embodiments of the invention the trisomy can be trisomy 21 [using e.g., the LSI 21q22 orange labeled probe (Abbott cat no. 5J13-02)], trisomy 18 [using e.g., the CEP 18 green labeled probe (Abbott Cat No. 5J10-18); the CEP® 18 (D18Z1, α satellite) Spectrum Orange™ probe (Abbott Cat No. 5J08-18)], trisomy 16 [using e.g., the CEP16 probe (Abbott Cat. No. 6J37-17)], trisomy 13 [using e.g., the LSI® 13 SpectrumGreen™ probe (Abbott Cat. No. 5J14-18)], and the XXY, XYY, or XXX trisomies which can be detected using e.g., the CEP X green and Y orange probe (Abbott cat no. 5J10-51); and/or the CEP®X SpectrumGreen™/CEP®Y (µ satellite) SpectrumOrange™ probe (Abbott Cat. No. 5J10-51).

Additional trisomies or partial trisomies which can be detected using chromosome-specific FISH probes, PRINS primers, Q-FISH and MCB staining include, but are not limited to, partial trisomy 1q32-44 (Kimya Y et al., Prenat Diagn. 2002, 22:957-61), trisomy 9p with trisomy 10p (Hengstschlager M et al., Fetal Diagn Ther. 2002, 17:243-6), trisomy 4 mosaicism (Zaslav A L et al., Am J Med. Genet.

2000, 95:381-4), trisomy 17p (De Pater J M et al., Genet Couns. 2000, 11:241-7), partial trisomy 4q26-qter (Petek E et al., Prenat Diagn. 2000, 20:349-52), trisomy 9 (Van den Berg C et al., Prenat. Diagn. 1997, 17:933-40), partial 2p trisomy (Siffroi J P et al., Prenat Diagn. 1994, 14:1097-9), partial trisomy 1q (DuPont B R et al., Am J Med. Genet. 1994, 50:21-7), and/or partial trisomy 6p/monosomy 6q (Wauters J G et al., Clin Genet. 1993, 44:262-9).

According to some embodiments of the invention, the chromosomal abnormality is a monosomy such as, monosomy 22, 16, 21 and 15, which are known to be involved in pregnancy miscarriage (Munne, S. et al., 2004. Reprod Biomed Online. 8: 81-90)].

According to some embodiments of the invention the monosomy can be monosomy X, monosomy 21, monosomy 22 [using e.g., the LSI 22 (BCR) probe (Abbott, Cat. No. 5J17-24)], monosomy 16 (using e.g., the CEP 16 (D16Z3) Abbott, Cat. No. 6J36-17) and monosomy 15 [using e.g., the CEP 15 (D15Z4) probe (Abbott, Cat. No. 6J36-15)].

According to some embodiments of the invention, the chromosomal abnormality can be a translocation, re-arrangement or microdeletion which is present in at least one of the conceptus parents. These include, but are not limited to the 15q11-q13 microdeletion which can give birth to a child with Angelman or Prader Willi syndrome (Erdel M et al., Hum Genet. 1996, 97: 784-93), mosaic for a small supernumerary marker chromosome (SMC) (Giardino D et al., Am J Med. Genet. 2002, 111:319-23); t(11; 14)(p15; p13) translocation (Benzacken B et al., Prenat Diagn. 2001, 21:96-8); unbalanced translocation t(8; 11)(p23.2; p15.5) (Fert-Ferrer S et al., Prenat Diagn. 2000, 20:511-5); 11q23 microdeletion (Matsubara K, Yura K. Rinsho Ketsueki. 2004, 45:61-5); Smith-Magenis syndrome 17p11.2 deletion (Potocki L et al., Genet Med. 2003, 5:430-4); 22q13.3 deletion (Chen C P et al., Prenat Diagn. 2003, 23:504-8); Xp22.3. microdeletion (Enright F et al., Pediatr Dermatol. 2003, 20:153-7); 10p14 deletion (Bartsch O, et al., Am J Med. Genet. 2003, 117A:1-5); 20p microdeletion (Laufer-Cahana A, Am J Med. Genet. 2002, 112:190-3.), DiGeorge syndrome [del(22) (q11.2q11.23)], Williams syndrome [7q11.23 and 7q36 deletions, Wouters C H, et al., Am J Med. Genet. 2001, 102:261-5.]; 1p36 deletion (Zenker M, et al., Clin Dysmorphol. 2002, 11:43-8); 2p microdeletion (Dee S L et al., J Med. Genet. 2001, 38:E32); neurofibromatosis type 1 (17q11.2 microdeletion, Jenne D E, et al., Am J Hum Genet. 2001, 69:516-27); Yq deletion (Toth A, et al., Prenat Diagn. 2001, 21:253-5); Wolf-Hirschhorn syndrome (WHS, 4p16.3 microdeletion, Rauch A et al., Am J Med Genet. 2001, 99:338-42); 1p36.2 microdeletion (Finelli P, Am J Med. Genet. 2001, 99:308-13); 11q14 deletion (Coupry I et al., J Med. Genet. 2001, 38:35-8); 19q13.2 microdeletion (Tentler D et al., J Med. Genet. 2000, 37:128-31); Rubinstein-Taybi (16p13.3 microdeletion, Blough R I, et al., Am J Med. Genet. 2000, 90:29-34); 7p21 microdeletion (Johnson D et al., Am J Hum Genet. 1998, 63:1282-93); Miller-Dieker syndrome (17p13.3), 17p11.2 deletion (Juyal R C et al., Am J Hum Genet. 1996, 58:998-1007); 2q37 microdeletion (Wilson L C et al., Am J Hum Genet. 1995, 56:400-7).

The invention according to some embodiments can be used to detect inversions [e.g., inverted chromosome X (Lepretre, F. et al., Cytogenet. Genome Res. 2003. 101: 124-129; Xu, W. et al., Am. J. Med. Genet. 2003. 120A: 434-436), inverted chromosome 10 (Helszer, Z., et al., 2003. J. Appl. Genet. 44: 225-229)], cryptic subtelomeric chromosome rearrangements (Engels, H., et al., 2003. Eur. J. Hum. Genet. 11: 643-651; Bocian, E., et al., 2004. Med. Sci. Monit. 10: CR143-CR151), and/or duplications (Soler, A., et al., Prenat. Diagn. 2003. 23: 319-322).

According to some embodiments of the invention, the DNA analysis can be Southern blot hybridization, direct sequencing of a PCR product [e.g., amplification of a genomic sequence using specific PCR primers followed by a sequencing reaction using, for example, the Applied Biosystems (Foster City, Calif.) ABI PRISM® BigDye™ Primer or BigDye™ Terminator Cycle Sequencing Kits], quantitative fluorescent PCR e.g., for chromosomes 13, 18, 21, X, Y [e.g., Aneufast kit (Genomed), Q-Star kit (Elucigene) with the needed modifications for a few cells or single cells], restriction fragment length polymorphism (RFLP) [e.g., RFLP on the genomic DNA using a labeled probe (i.e., Southern Blot RFLP) or on a PCR product (i.e., PCR-RFLP)], allele specific oligonucleotide (ASO) [e.g., by hybridization with radioactively labeled allelic specific oligonucleotides (ASO) on genomic DNA (see Conner et al., Proc. Natl. Acad. Sci., 80:278-282, 1983) or on PCR products (see e.g., Kerem B, et al., 1990, Proc. Natl. Acad. Sci. USA, 87:8447-8451), allele-specific PCR [e.g., as described for the cystic fibrosis Q493X mutation in Kerem B, 1990 (Supra)], methylation-specific PCR (MSPCR) [by treating the DNA with sodium bisulfite which converts the unmethylated, but not the methylated, cytosine residues to uracil, followed by PCR amplification as described in Buller A., et al., 2000, Mol. Diagn. 5: 239-43], Pyrosequencing™ analysis (Pyrosequencing, Inc. Westborough, Mass., USA), Acycloprime™ analysis (Perkin Elmer, Boston, Mass., USA), reverse dot blot, dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the TaqMan system (Holland, P. M. et al., 1991. Detection of specific polymerase chain reaction product by utilizing the 5'→3' exonuclease activity of *Thermus aquaticus* DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S, and Higuchi, R. Single-tube genotyping without oligonucleotide probes. Genome Res. 9:72-78 (1999)], FRET primers (Solinas A et al., 2001. Nucleic Acids Res. 29: E96), AlphaScreen (Beaudet L, et al., Genome Res. 2001, 11(4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut I G. 2003. Rapid Commun. Mass. Spectrom. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab. Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu T M, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi M M. 2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) and MassArray (Leushner J, Chiu N H, 2000. Mol. Diagn. 5: 341-80).

Nucleic acid substitutions can be also identified in mRNA molecules derived from the isolated trophoblast cell of the present invention. Such mRNA molecules are first subjected to an RT-PCR reaction following which they are either directly sequenced or subjected to any of the DNA analysis methods described hereinabove.

According to some embodiments of the invention, the DNA analysis can identify an abnormality in the fetal DNA or determine the paternity of the fetus. DNA abnormality can be a single nucleotide substitution (e.g., which causes a disease or comprises a polymorphism), DNA re-arrangments, inversion, deletion, duplication, insertion, micro-deletion, micro-insertion, short deletion, short insertion, multinucleotide substitution, abnormal DNA methylation and loss of imprint (LOI).

For example, a DNA abnormality can be associated with genetic disease such as a single-gene disorder or recessive disorders, which can be tested prenatally if both parents are carriers [e.g., cystic fibrosis, Canavan's Disease, Tay-Sachs disease, Gaucher disease, Familial Dysautonomia, Niemann-Pick disease (AB), Fanconi anemia (Fanconi-C, Fanconi-A), Ataxia telaugiestasia, Bloom's syndrome, Familial Mediterranean fever (FMF), X-linked spondyloepiphyseal dysplasia tarda, factor XI, Mucolipidosis 4, Usher syndrome I, Glycogen storage disease type I, Glycogen storage disease type III, Maple syrup urine disease, Spinal muscular atrophy (SMA), Nemalin, Gaucher type I, Alpha anti trypsin deficiency, Ataxia Telangiectasis, Limb girdle muscular disease 2B, MLC-1, Costaf's disease, Phenylketonuria, Metachromatic leukodystrophy], sex linked disorders (e.g., Fragile X, Hemophilia) an imprinting disorder [e.g., Angelman Syndrome, Prader-Willi Syndrome, Beckwith-Wiedemann syndrome, Myoclonus-dystonia syndrome (MDS)], predisposition to various cancer diseases (e.g., mutations in the BRCA1 and BRCA2 genes), dominant disorders (e.g., Huntington's disease, Marfan's syndrome, Cadasil), as well as disorders which are caused by minor chromosomal aberrations (e.g., minor trisomy mosaicism, duplication sub-telomeric regions, interstitial deletions or duplications) which are below the detection level of conventional in situ chromosomal and/or DNA analysis methods (i.e., FISH, Q-FISH, MCB and PRINS).

As used herein, the phrase "paternity" refers to the likelihood that a potential father of a specific conceptus is the biological father of that conceptus.

Determining the paternity of a conceptus can be performed by subjecting the trophoblast cell DNA to a PCR-based or RFLP analyses (Strom C M, et al., Am J Obstet Gynecol. 1996, 174: 1849-53; Yamada Y, et al., 2001. J Forensic Odontostomatol. 19: 1-4) and comparing the conceptus polymorphic markers [e.g., substitution, deletion, insertion, inversion, variable number of tandem repeats (VNTR), short tandem repeats (STR), minisatellite variant repeats (MVR)] to a set of polymorphic markers obtained from a potential father.

For example, polymorphic markers used in paternity testing include the minisatellite variant repeats (MVR) at the MS32 (D1S8) or MS31A (D7S21) loci (Tamaki, K et al., 2000, Forensic Sci. Int. 113: 55-62)], the short tandem repeats (STR) at the D1S80 loci (Ceacareanu A C, Ceacareanu B, 1999, Roum. Arch. Microbiol. Immunol. 58: 281-8], the DXYS156 loci (Cali F, et al., 2002, Int. J. Legal Med. 116: 133-8), the "myo" and PYNH24 RFLP-probes [Strom C M, et al., (Supra) and Yamada Y, et al., (Supra)] and/or oligotyping of variable regions such as the HLA-II (Arroyo E, et al., 1994, J. Forensic Sci. 39: 566-72).

According to some embodiments of the invention, the DNA analysis comprises comparative genome hybridization (CGH).

Comparative Genome Hybridization (CGH) is based on a quantitative two-color fluorescence in situ hybridization (FISH) on metaphase chromosomes. In this method a test DNA (e.g., DNA extracted from the trophoblast cell of the present invention) is labeled in one color (e.g., green) and mixed in a 1:1 ratio with a reference DNA (e.g., DNA extracted from a control cell) which is labeled in a different color (e.g., red). Methods of amplifying and labeling whole-genome DNA are well known in the art (see for example, Wells D, et al., 1999; Nucleic Acids Res. 27: 1214-8). Briefly, genomic DNA is amplified using a degenerate oligonucleotide primer [e.g., 5'-CCGACTCGAGNNNNNNATGTGG; SEQ ID NO:24 (Telenius, H., et al., 1992; Genomics 13:718-25)] and the amplified DNA is labeled using e.g., the Spectrum Green-dUTP (for the test DNA) or the Spectrum Red-dUTP (for the reference DNA). The mixture of labeled DNA samples is precipitated with Cot1 DNA (Gibco-BRL) and resuspended in an hybridization mixture containing e.g., 50% formamide, 2×SSC, pH 7 and 10% dextrane sulfate. Prior to hybridization, the labeled DNA samples (i.e., the probes) are denatured for 10 minutes at 75° C. and allowed to cool at room temperature for 2 minutes. Likewise, the metaphase chromosome spreads are denatured using standard protocols (e.g., dehydration in a series of ethanol, denaturation for 5 minutes at 75° C. in 70% formamide and 2×SSC). Hybridization conditions include incubation at 37° C. for 25-30 hours in a humidified chamber, following by washes in 2×SSC and dehydration using an ethanol series, essentially as described elsewhere (Wells, D., et al., 2002; Fertility and Sterility, 78: 543-549). Hybridization signal is detected using a fluorescence microscope and the ratio of the green-to-red fluorescence can be determined using e.g., the Applied Imaging (Santa Clara, Calif.) computer software. If both genomes are equally represented in the metaphase chromosomes (i.e., no deletions, duplication or insertions in the DNA derived from the trophoblast cell) the labeling on the metaphase chromosomes is orange. However, regions which are either deleted or duplicated in the trophoblast cell are stained with red or green, respectively.

According to some embodiments of the invention, the metaphase chromosomes used by the CGH method are derived from a reference control cell (i.e., a normal individual) having a karyotype of either 46, XY or 46, XX.

DNA array-based comparative genomic hybridization (CGH-array), which is described in Hu, D. G., et al., 2004, Mol. Hum. Reprod. 10: 283-289, is a modified version of CGH and is based on the hybridization of a 1:1 mixture of the test and reference DNA probes on an array containing chromosome-specific DNA libraries. Methods of preparing chromosome-specific DNA libraries are known in the art (see for example, Bolzer A., et al., 1999; Cytogenet. Cell. Genet. 84: 233-240). Briefly, single chromosomes are obtained using either microdissection or flow-sorting and the genomic DNA of each of the isolated chromosomes is PCR-amplified using a degenerated oligonucleotide primer. To remove repetitive DNA sequences, the amplified DNA is subjected to affinity chromatography in combination with negative subtraction hybridization (using e.g., human Cot-1 DNA or centromere-specific repetitive sequence as subtractors), essentially as described in Craig J M., et al., 1997; Hum. Genet. 100: 472-476. Amplified chromosome-specific DNA libraries are then attached to a solid support [(e.g., SuperAmine slides (TeleChem, USA)], dried, baked and washed according to manufacturer's recommendation. Labeled genomic DNA probes (a 1:1 mixture of the test and reference DNAs) are mixed with non-specific carrier DNA (e.g., human Cot-1 and/or salmon sperm DNA, Gibco-BRL), ethanol-precipitated and re-suspended in an hybridization buffer such as 50% deionized formamide, 2×SSC, 0.1% SDS, 10% Dextran sulphate and 5×Denhardt's solution. The DNA probes are then denatured (80° C. for 10 minutes), pre-annealed (37° C. for 80 minutes) and applied on the array for hybridization of 15-20 hours in a humid incubator. Following hybridization the arrays are washed twice for 10 minutes in 50% formamide/2×SSC at 45° C. and once for 10 minutes in 1×SSC at room temperature, following which the arrays are rinsed three times in 18.2 MΩ deionized water. The arrays are then scanned using any suitable fluorescence scanner such as the GenePix 4000B microarray reader (Axon Instruments, USA) and analyzed using the GenePix Pro. 4.0.1.12 software (Axon).

The DNA-based CGH-array technology was shown to confirm fetal abnormalities detected using conventional G-banding and to identify additional fetal abnormalities such as mosaicism of trisomy 20, duplication of 10q telomere region, interstitial deletion of chromosome 9p and interstitial duplication of the PWS region on chromosome 15q (Schaeffer, A. J., et al., 2004; Am. J. Hum. Genet. 74: 1168-1174), unbalanced translocation (Klein O D, et al., 2004, Clin Genet. 65: 477-82), unbalanced subtelomeric rearrangements (Ness G O et al., 2002, Am. J. Med. Genet. 113: 125-36), unbalanced inversions and/or chromosomal rearrangements (Daniely M, et al., 1999; Cytogenet Cell Genet. 86: 51-5).

According to some embodiments of the invention, the method of prenatally diagnosing a conceptus further comprising culturing the trophoblast prior to step (b) under conditions suitable for proliferation of the trophoblast.

It should be noted that in order to culture the trophoblast in vitro the cell's viability should be preserved following the identification/isolation processes. Those of skills in the art are capable of selecting conditions and assays which can preserve cell viability (e.g., using protein detection methods such as immunofluorescence followed by FACS or MACS isolation).

Thus, an isolated trophoblast cell(s) can be cultured in a tissue culture medium [e.g., BioAMF-2 complete medium, 01-194-1, Biological Industries, Beit Haemek; Chang Medium, Irvine Diagnostics (e.g., CHANG MEDIUM® BMC 91004; CHANG MEDIUM® MF, 91005; CHANG MEDIUM® D with Antibiotics, 99404; CHANG MEDIUM® C with Antibiotics Lyophilized, 99419)] for 4-10 days in a tissue culture incubator [such as Hereus, Tuttenauer] at a temperature of about 37° C. According to some embodiments of the invention, the trophoblast cells are cultured in chamber slides (for example, Nunc Lab-Tek II chamber slide 154526) which are suitable for subsequent conceptus diagnostic assay(s).

According to some embodiments of the invention, the trophoblast culture comprises at least about 5 times more trophoblasts than a non-cultured trophoblast-containing biological sample.

According to some embodiments of the invention, the conceptus diagnostic assay comprises karyotype analysis (e.g., a photomicrograph of an individual's chromosomes showing the number, size, and shape of each chromosome type).

According to some embodiments of the invention, karyotype analysis is performed using a staining method such as G-banding (Giemsa stain), Q-banding (Quinacrine mustard stain), R-banding (reverse-Giemsa), and C-banding (centromere banding).

Thus, the teachings of the invention can be used to identify chromosomal and/or DNA aberrations in a conceptus, and/or determine the paternity of a conceptus without subjecting the mother to invasive and risk-carrying procedures.

The agents described hereinabove for detecting the expression of the annexin IV, cytokeratin-7, cytokeratin-8 and cytokeratin-19 trophoblast marker (e.g., the antibodies directed against the trophoblast markers, the polynucleotide probes capable of specifically hybridizing to the trophoblast marker RNAs, e.g., the polynucleotide probes set forth by SEQ ID NOs:12, 13, 14 or 15, the PCR primers capable of amplifying the trophoblast markers cDNA, such as those set forth by SEQ ID NOs:16-17, 18-19, 20-21 or 22-23) and the reagents for conceptus diagnosis as described above (e.g., a reagent such as a polynucleotide probe, PCR primer(s) which is used in FISH, PRINS, MCB, Q-FISH, CGH, CGH-array, DNA analysis and paternity testing) may be included in a diagnostic kit/article-of-manufacture. According to some embodiments of the invention, the diagnostic kit/article-of-manufacture further comprises instructions and labels indicating FDA approval for use in prenatally diagnosing a conceptus or for a pregnancy test.

Such a kit can include, in separate containers at least one of the above described trophoblast identifying agents (e.g., anti annexin IV antibody, or a polynucleotide probe capable of specifically hybridizing to the annexin IV mRNA) packed on one container and at least one of the above described conceptus diagnostic reagents (e.g., FISH probes) packed in second container. The kit may further include imaging agents such as enzymes, secondary antibodies, buffers, chromogenic substrates, fluorogenic material packed in an additional container. The kit may also include appropriate buffers and preservatives for improving the shelf-life of the kit.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Proteomic Analysis

Preparation of Blood Samples—Blood Samples were Separated by Single Density gradient centrifugation (1.077 g/ml) in Unisep tubes (Nova-med u-16) for 20 minutes at 1000 g at room temperature. The top cell layer containing mononuclear cells was collected and washed twice in phosphate buffered saline (PBS; Biological industries Israel Beit Haemek 020231A) containing 0.1% Bovine Serum Albunin-BSA (Sigma Aldrich A-9418). The cells were counted using a hemacytometer (Fisher 0267110). $1\times10^6$ cells derived from each sample was deposited onto two positively charged glass slides (Biogenex super frost plus slides Menzel-Glaser MG051101) by centrifugation (Shandon Cytospin-3) and the remainder of the sample was flash-frozen in liquid nitrogen and stored at −70° C. In order to estimate the level of "contamination" of the sample with red blood cells (erythrocytes) DAB-3,3' diaminobenzidine tetrahydrochloride chemical staining (Sigma Aldrich D-6190) which identifies hemoglobin was performed according to the manufacturer's recommended protocol and subsequently the slides were washed and stained with Hematoxylin (Merck 1.09253.0500).

Trophoblast isolation and purification—Trophoblasts were isolated from fresh first trimester placentas as previously described by Blaschitz et al 1996. In short, the procedure included enzymatic digestion using combination of Trypsin solution 0.25% (Gibco 2550) and DNAse I (Sigma Aldrich D-4513) followed by Percoll (Sigma Aldrich P-1644) density gradient centrifugation (1.124 g/ml). This gradient separates the trophoblast cells into seven different layers. The trophoblasts cells were enriched by negative magnetic cell sorting (Dynal Biotech MPC-L 120.21) using anti-CD-45RB antibody (DAKO M0833) and anti-CD-90-Fibroblasts antibody (Dianova DIA 100). The antibodies were incubated with Sheep anti-mouse magnetic beads (Dynal Biotech 110.31). The cell tube was attached to a magnetic field. The magnetically labeled (non-trophoblast) cells were drawn to the magnet whereas the non-magnetically labeled (presumably trophoblast) cells remained in the solution and were collected in a separate tube. $1\times10^5$ cells derived from each sample was deposited onto two positively charged glass slides (Biogenex super frost plus slides Menzel-Glaser MG051101) by centrifugation (Shandon Cytospin-3) and the remainder of the sample was flash-frozen in liquid nitrogen and stored at −70° C. The trophoblast cells were identified by immunofluorescent staining which recognizes cells expressing primary antigen CytoKeratin-7 (DAKO M701801). The cells were labeled with a mouse anti human monoclonal antibody against CK7, clone OV-TL12/30, at a 1:100 dilution in PBS/ 0.1% BSA for 30 minutes at room temperature and stained with secondary fluorescent antibody Donkey anti mouse (Chemicon clone LP5K), at a 1:100 dilution in PBS/0.1% BSA for 30 minutes at room temperature. In order to estimate the extent of fibroblast contamination the isolated cells were incubated with monoclonal antibodies against Vimentin (DAKO clone V9 M0725) at a 1:100 dilution in PBS/0.1% BSA for 30 minutes at room temperature and with secondary fluorescent antibody Donkey anti mouse (Chemicon CBL194F), at a 1:100 dilution in PBS/0.1% BSA for 30 minutes at room temperature.

Two dimensional polyacrylamide gel electrophoresis (2-D PAGE)—Isoelectric focusing was performed with commercially available IPG-strips (Amersham Biosciences:18 cm, pH 4-7). Samples were loaded by rehydration for 24 hours in solution containing lysis buffer (7 M urea Applichem Biochemica, Darmstadt, Germany) 2 M thiourea Sigma Aldrich), 0.2 M dimethylbenzyl-ammonium propan sulfonate (NDSB, ICN Biomedicals, Eschwege, Germany), 1% dithiothreol (DTT) (Applichem), 4% CHPS (Applichem), 0.5% Pharmalytes (Amersham Biosciences, Freiburg Germany) and a trace of the dye bromophenol blue (Serva Heidelberg Germany). The isoelectric focusing was preformed with the multiphorll unit (Amersham Biosciences). The separation in the second dimension was performed in polyacrylamide gels of 12.5% T and 2.6% C on the investigator 2-D electrophoresis system (Genomic solutions) with approximately 2 W per gel. Analytical and preparative gels were loaded with 100 and 800 μg of crude protein extract, respectively. Analytical gels were stained with Coomassie Blue.

Quantitative image analysis—The quantitative analysis of the 2-D PAGE images was performed with the Z3 software (Compugen, Tel Aviv Israel), using the Raw master Gel (RMG) option to create a synthetic gel. Spot volume was calculated by a multiplication of the spot area with its intensity. Normalization of the spot volumes for comparison between different gels was done by the Total Spot Volume method. In this method, the total volume of all spots in the gel divides the volume of each spot.

Protein identification—The identification was performed with the spot isolated from Coomassie blue stained gels. It was accomplished by mass spectrometry, according to established protocols as describe previously by Bandow et al., 2003 (Bandow J E, Becher D, Büttner K, Hochgräfe F, Freiberg C, Brötz H, Hecker M. The role of peptide deformylase in protein biosynthesis: a proteomic study. Proteomics. 2003 (3):299-306). Briefly protein spots were excised from stained 2-D gels, the pieces were washed and extracted from the gel by diffusion and then the peptides were eluted and put onto a sample plate for MALDI-MS. Peptide masses were determined in the positive ion reflector mode in a Voyager-DE STR mass spectrometer (Applied Biosystems) with internal calibration. Peptide mass fingerprints were compared to databases using the MS-Fit program (Hyper Text Transfer Protocol://prospector (dot) ucsf (dot) edu). The searches took into consideration oxidation of methionine, pyroglutamic acid, formation at the N-terminal glutamine and modification of cytosine by carbamidomethylation or acrylamide, as well as partial cleavage leaving one internal cleavage site Primary Antibodies—mouse anti-human cytokeratin 8 clone LP3K (Serotec, Raleigh, N.C., USA; Catalogue number 0200-0618), mouse anti-human cytokeratin 19 clone RCK 108 (Dako Corp, Carpenteria, Calif., USA; Catalogue number M0888), Goat anti-hemoglobin zeta polyclonal antibody clone C-16 (Santa Cruz Biotechnology, Inc., Santa Cruz, Calif., USA; Catalogue number sc-22723), mouse anti-annexin IV clone D2 (Santa cruz Biotechnology, Inc., Santa Cruz, Calif., USA; Catalogue number sc-46693), mouse anti-human cytokeratin-7 clone OV-TL12/30 (Dako Corp, Carpenteria, Calif., USA; Catalogue number M701801). All antibodies were diluted 1:50 in PBS (Biological Industries 02-023-1A) containing 0.1% bovine serum albumin (BSA; fraction V, Sigma St Louis, Mo., USA, Catalogue number A941B).

Secondary antibodies—(FITC)-labeled donkey-anti mouse F(ab')$_2$ (Jackson ImmunoResearch Europe Ltd. Suffolk, UK; Catalogue number 715-096-151; FITC labeled Donkey anti mouse (Jackson ImmunoResearch Laboratories 715-095-151.

Annexin IV-based magnetic cell sorting (MACS) enrichment of trophoblasts from maternal blood—Density gradient centrifugation of heparinized maternal blood samples (20 ml blood samples) was carried out with Unisep Maxi tubes (Novamed Jerusalem, Israel, U16 tubes). The Buffy-coat layer of cells was washed, counted (about $1$-$5 \times 10^7$ nucleated cells were obtained from a 20 ml blood sample) and contacted with an anti-annexin IV monoclonal antibody (diluted 1:50 in 200 μl of PBS containing 0.1% BSA) by incubating the cells with the anti-annexin IV antibody for 30 minutes at room temperature while shaking. 500 μl of MACS buffer were added and the cells were then centrifuged (10 minutes at 300 g) and excess of unbound first antibody (anti-annexin IV) was removed. For labeling of anti-annexin positive cells, a secondary antibody, fluorescein isothiocyanate (FITC)-labeled donkey-anti mouse F(ab')2 (Jackson ImmunoResearch Europe Ltd. Suffolk, UK; Catalogue number 715-096-151) diluted 1:50 in 200 μl of PBS containing 0.1% BSA was added for a 30-minute incubation while shaking. The MACS buffer (500 μl) was added to the cells which were further centrifuged (10 minutes at 300 g) and excess of unbound secondary antibody (FITC donkey anti-mouse) was removed. For magnetic beads enrichment, 20 μl of the anti FITC monoclonal antibody coupled to magnetic beads (FITC-beads; Miltenyi Biotec, Bergisch Gladbach, Germany, 130-048-701) diluted in 80 μl of a MACS buffer [PBS at PH 7.2 (Biological Industries 02-023-1A) containing 0.5% BSA (Sigma Aldrich A-9418) and 2 mM EDTA (Sigma Aldrich E-7889)] were added to the cells and incubated for 15 minutes at 4° C. 500 μl MACS buffer were added and the cells were then centrifuged (10 minutes at 310 g) to remove excess of unbound beads and resuspended in 500 μl MACS buffer. The cells were then loaded on Mini-Macs© columns (Miltenyi Biotec, 130-042-201) and MACS-positive cells were eluted according to the manufacturer's recommended protocol. MACS-positive cells were counted and re-suspended in 250 μl of PBS/0.1% BSA followed by cyto-centrifugation (using the Shandon cytospin 3, Thermo Fisher Scientific, Inc. Waltham, Mass. USA) onto microscope slides as previously described (Guetta et al., 2005). Annexin-IV-labeled cells were observed by following the FITC fluorescence using a fluorescent microscope (Zeiss).

Alternatively, the Buffy-coat cells (about $1$-$5 \times 10^7$ nucleated cells) were incubated with the primary antibody [Annexin-IV antibody (diluted 1:50 in 200 μl of PBS containing 0.1% BSA, 30 minutes at room temperature while shaking)], washed (by centrifugation for 10 minutes at 300 g), and further incubated with 20 μl of secondary antibody coupled to beads (goat anti-mouse coupled to magnetic beads Miltenyi Biotec 130-048-40280) and 80 μl of MACS buffer for a 15 minute incubation at 4° C. The excess of beads was then removed as described above and the MACS protocol with Mini-Macs© columns (130-042-201, Miltenyi Biotec) was performed. Slides were prepared with the MACS-positive cells and were further subjected to immunofluorescence and/or FISH analyses.

Protocol for MACS enrichment of trophoblasts from maternal blood with intercellular antigens—The protocol was developed with CK-7 antibodies, however it can be applied with additional antibodies directed against intracellular antigens. Blood samples were separated as described above (using the density gradient centrifugation with Unisep Maxi tubes), nucleated cells were fixed in 1 ml 1.5% paraformaldyhyde (Sigma, F-1635) for one hour at room temperature with shaking, followed by centrifugation at 300 g for 10 minutes, washed with 1 ml PBS containing 0.5% BSA and centrifuged (300 g for 10 minutes). 100 μl of FcR blocking agent (Miltenyi Biotech, 130-059-901) and the primary antibody [e.g., anti CK-7, mouse anti-human cytokeratin-7 clone OV-TL12/30 (Dako Corp, Carpenteria, Calif., USA; Catalogue number M701801)] diluted 1:50 in PBS/0.5% fetal bovine serum/0.3% Saponin (Sigma, S-4521) were added to the cells for a 30-minute incubation at room temperature (RT) with shaking. The cells were then centrifuged at 300 g for 10 minutes washed in 1 ml PBS/0.1% BSA and centrifuged again. 20 μl of a secondary antibody coupled to beads (Goat-anti mouse microbeads, Miltenyi Biotec130-048-402) diluted in 80 μl of a MACS buffer was added for a 30-minute incubation at 4° C. After adding 500 μl of MACS buffer, the excess of beads was then removed (by centrifugation for 10 minutes at 300 g) and the MACS protocol with Mini-Macs© columns (130-042-201, Miltenyi Biotec) was performed. MACS-positive cells were further cyto-centrifuged as described above and were subjected to immunofluorescence using e.g., anti-CK-7 antibody followed by a secondary FITC-labeled antibody as described above and/or FISH analysis.

Immunofluorescence following MACS enrichment—The Primary antibody-mouse anti-human cytokeratin-7 clone OV-TL12/30 (Dako Corp, Carpenteria, Calif., USA; Catalogue number M701801) was diluted 1:50 in PBS/0.5% Fetal Bovine serum/0.3% Saponin (Sigma, S-4521). After fixation in acetone (Merck 1.00014.2500) for 15 minutes the slides were rinsed twice for 5 minutes in PBS and incubated at room temperature for 30 minutes with anti-cytokeratin 7 antibody. Subsequently, all the slides were washed 2 times for 5 minutes in PBS and the detection was preformed by incubating the slides with the FITC labeled Donkey anti mouse (Jackson ImmunoResearch Laboratories 715-095-151; diluted 1:50 in PBS/0.1% BSA) for 30 minutes at room temperature. Subsequently, cells were washed 2 times for 5 minutes in PBS. The slides were then dried and stained with DAPI (Vector, H-1200).

Microscope analysis—Analysis of slides after immunofluorescent staining was performed with a fluorescent microscope (Zeiss Axioscope fluorescent microscope). The positive cells were identified by green (FITC) cytoplasmic staining and the nuclei were counter-stained with DAPI (Vector). The number of positive cells was counted and their percentage among the total number of cells on the slide was calculated. Photomicrographs were prepared with Cytovision software (Applied Imaging).

Fluorescent in situ hybridization (FISH) following MACS enrichment—Slides were fixed in methanol: acetic acid (3:1) twice by two 15 minute incubations, at room temperature, washed in PBS and dehydrated at −20° C., in 70% 90% and 100% ethanol solutions, 2 minutes each. Slides were denatured in 70% de-ionized formamide (Sigma) in 2×SSC (2× sodium citrate chloride) at 75° C. for 5 minutes, dehydrated in alcohol as described above and transferred to a hotplate (56° C.). X-chromosome centromere enumeration probe (CEP) and Y heterochromatin sat III or Y CEP probe (Vysis, Downer's Grove, Ill., USA) were mixed with hybridization buffer supplied by manufacturer and denatured for 5 minutes at 75° C. Probe mixture (5 μl) was applied over the cell-containing area and covered with a round coverslip (12 mm diameter). Hybridization was carried out in a moist chamber at 37° C. for 4 hours, the coverslips were removed and the slides were washed in 0.4×SSC/0.03% NP40 (NP-40 Fluka Biochemika 74388) at 74° C. for 2 minutes and in 2×SSC/0.01% NP40 for 2 minutes at room temperature. Vectashield anti-fade (H-1200Vector, Burlinghame, Calif.) containing 4,6-diamino-2-phenylindole dihydrochloride (DAPI) DNA staining reagent was added to slides after washing steps and air drying at room temperature.

Example 1

Identification of New Trophoblast-Specific Proteins by Comparative Proteomics

Experimental Results

Preparation of trophoblasts and peripheral blood cell samples for two-dimensional (2-D) gel electrophoresis—Trophoblast and peripheral blood cell samples were obtained from women, undergoing pregnancy termination in the first trimester. Trophoblasts were isolated from placental tissue following pregnancy termination carried out under social indications. The purity of the isolated trophoblast preparations was high (85-94% positive cells), with low fibroblast contamination (0-12%—positive cells).

Identification of proteins with unique expression pattern in trophoblasts as compared to peripheral blood samples—Isolation and identification of proteins was performed by proteomics technology. The results of 2-D gel analysis (FIG. 1) revealed many differences in protein expression between the maternal blood cells and placenta-derived trophoblasts. The most prominent protein spots that appeared in the placenta samples but were absent in the blood samples were isolated, purified and identified. The proteins identified were: cytokeratin 7 (GenBank Accession No. NP_005547; GI No. 30089956; SEQ ID NO:1), cytokeratin 8 (GenBank Accession No. NP_002264; GI No. 450-4919; SEQ ID NO:2), cytokeratin 19 (GenBank Accession No. NP_002267; GI No. 24234699; SEQ ID NO:3), Zeta globin (GenBank Accession No. NP_005323; GI No. 4885397; SEQ ID NO:4), A-gamma globin (GenBank Accession No. NP_000550; GI No. 28302131; SEQ ID NO:5), G-gamma globin (GenBank Accession No. NP_000175; GI No. 6715607; SEQ ID NO:6) and annexin IV (GenBank Accession No. NP_001144; GI No. 4502105; SEQ ID NO:7). Since Zeta globin, A-gamma globin and G-gamma globin are also expressed in fetal blood cells these proteins cannot be considered as "trophoblast-specific". Moreover, A-gamma globin and G-gamma globin are also expressed in maternal cells, thus not "fetal-specific".

Validation in placental sections—Validation of the expression pattern of the newly-identified trophoblast-specific markers was carried out in the JAR (ATCC catalog number HTB-144) and BeWo (ATCC catalog number CCL-98) trophoblast cell lines, as well as in-situ in first trimester placental sections using antibodies against cytokeratin 7 (an intracellular antigen), cytokeratin 8 (an intracellular antigen), cytokeratin 19 (an intracellular antigen) and annexin IV (a cell-surface antigen). All markers were found to be expressed in trophoblast cell lines as well as placental sections, confirming that they are suitable markers for trophoblast retrieval from maternal blood. It was noted that cytokeratin 7 staining was stronger than Annexin IV staining (FIGS. 2a-l).

These results demonstrate the identification of new trophoblast-specific markers which can be used to identify fetal cells in the maternal blood.

Example 2

Enrichment of the Rare Trophoblast Cells from the Maternal Blood Using Annexin IV—Based Macs Experimental Results Annexin-IV-based MACS on maternal blood samples—As is shown in FIG. 3, the annexin-IV-based magnetic cell sorting (MACS) of a maternal blood sample revealed a species of rare large cells which are positively stained with the annexin IV antibody.

FISH analysis of annexin IV-based MACS—Samples from females carrying a male fetus were subjected to magnetic cell sorting with an anti-annexin antibody. The MACS isolated cells were deposited on microscope slides using a cytospin (Shandon) as previously described (Guetta et al., 2005) and were further subjected to fluorescent in-situ hybridization (FISH) using the X and Y-chromosome-specific probes (Vysis) as previously described (Guetta et al., 2005). Fetal cells were identified according to the presence of one X and one Y-positive signal in the nucleus (FIG. 4).

These results demonstrate that fetal cells can be isolated from the maternal blood and be subject to conceptus diagnosis such as DNA analysis for the identification of single-gene diseases in fetuses of carrier parents; quantitative PCR analysis for the detection of aneuploidy; FISH or in vitro expansion for karyotype analysis.

Example 3

Validation of the Mew Trophoblast-Specific Markers in the Maternal Blood

Experimental Results

Validation in maternal blood samples—Twenty maternal blood samples were tested for presence of Annexin IV-positive cells using annexin IV-based MACS enrichment with FITC secondary antibody followed by anti FITC microbeads as described above. An average of 6.25 Annexin IV-positive cells were detected in each blood sample of 20 ml. Positive cells were detected in 90% of the samples (FIGS. 5a-c).

The fetal origin of cells enriched by MACS with Annexin IV protocol was tested in 12 samples from females carrying male fetuses. FISH was carried out with sex chromosome probes and cells exhibiting one X and one Y signal were considered of a fetal origin. An average of 4.8 fetal cells were detected in each maternal blood sample of 20 ml. 92% of the samples tested positive for fetal cells (FIG. 5d). In one sample, no fetal cells were detected.

Example 4

Development of an Enrichment Protocol Using Antibodies Recognizing Intracellular Antigens Cytokeratin 7, cytokeratin 8 and cytokeratin 19 are intracellularly expressed proteins. Therefore, modifications of the MACS protocol must be made in order to allow the enrichment of fetal cells using antibody-based MACS. The present inventors have developed a novel protocol for MACS using antibodies directed against intracellular proteins (described under "General Materials and Experimental Methods" hereinabove).

Enrichment of trophoblasts from blood samples using CK-7 based MACS—Experiments with mononuclear blood samples artificially spiked with trophoblast cell lines were applied in order to test the protocol which was optimized for the CK7 marker. FIGS. 6a-b demonstrate representative images of cell samples containing maternal and trophoblast cells.

Validation of the CK-7 based MACS protocol in blood samples of pregnant females—Subsequently, the protocol was tested in 12 maternal blood samples of pregnant females. Following CK7-based MACS, positive cells were identified either by FISH or fluorescent staining in 91.5% ($11/12$) of the samples (FIGS. 7a-b). In one sample, no FISH-fetal staining was observed.

Comparison of the new enrichment protocol of the invention to enrichment using available kit/protocols—Magnetic enrichment of cells expressing intracellular markers CK7 and CK8 was performed using the carcinoma cell enrichment and detection kit manufactured by Miltenyi catalogue #130-060-30). Four out of four maternal blood samples included cells which were positive for combined CK7 and CK-8 staining (range 2-8 cells per 20-ml blood sample, average 4). In contrast, in the protocol developed by the present inventors, the average number of CK-7 positive cells was 14, and the range was 4-36 in ⅝ samples processed with the immunofluorescence protocol described above.

Thus, these results demonstrate that Annexin IV and/or CK-7 are efficient markers for trophoblast enrichment from maternal blood cells. In addition, these results demonstrate the development of a new method of MACS enrichment using antibodies directed against intracellular antigens.

Example 5

Annexin IV is More Efficient than HLA-G in Isolating Trophoblast Cells from the Maternal Blood As is shown in FIG. 8, applying the novel Annexin IV marker for trophoblast enrichment in 20 samples of maternal blood yielded 4-fold more fetal cells (i.e., 6.25 cells per 20 ml blood sample) as compared to the HLA-G marker (i.e., 1.5 cells per 20 ml blood sample). In addition, the success rate of isolating trophoblast cells from the maternal blood was 18/20 using the Annexin IV-based MACS, as compared to 10/13 using the HLA-G-based MACS.

These results demonstrate that the new trophoblast specific marker can increase the efficiency of detection of fetal cells from the maternal blood.

Example 6

Trophoblasts Isolated from Maternal Blood Exhibit A Proliferative Capacity

The present inventors have previously showed that trophoblasts which are HLA-G positive can proliferate in culture for at least 5-7 days (Guetta E., et al., J. Histochemistry and Cytochemistry, 53: 337-339, 2005).

In the present study, trophoblasts which were enriched from maternal blood cells using an anti HLA-G antibody, were shown to have a proliferation capacity as illustrated by the metaphase chromosomes (FIG. 9).

Enrichment of trophoblasts cells from the maternal using the Annexin IV antibody (which was shown to be more efficient than the HLA-G antibody, see FIG. 8, Example 6 above) followed by culturing of the cells in vitro under conditions favoring trophoblast expansion, is expected to result in a higher yield of trophoblast proliferating cells. Such cells can be used for a subsequent karyotype analysis and prenatal diagnosis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

PCT Publication No. WO2006/018849

Bianchi D W, Zickwolf G K, Weil G J, Sylvester S, DeMaria M A. Male fetal progenitor cells persist in maternal blood for as long as 27 years postpartum. Proc. Natl. Acad. Sci. U S A. 1996, 93(2):705-8.

Daya, D. and Sabet, L. The use of cytokeratin as a sensitive and reliable marker for trophoblastic tissue. Am. J. Clin. Pathol. 1991, 95: 137-141.

Guetta E, Gutstein-Abo L., Barkai G. Trophoblasts isolated from the maternal circulation: In-vitro expansion and potential application in non-invasive prenatal diagnosis. J. Histochem. Cytochem. 2005, 53:337-339.

Guetta E, Simchen M J, Mammon-Daviko K, Gordon D, Aviram-Goldring A, Rauchbach N, Barkai G. Analysis of fetal blood cells in the maternal circulation: challenges, ongoing efforts, and potential solutions. Stem Cells Dev. 2004, 13:93-99.

Guetta E, Gordon D, Simchen M J, Goldman B, Barkai G Hematopoietic progenitor cells as targets for non-invasive prenatal diagnosis: detection of fetal CD34+ cells and assessment of post-delivery persistence in the maternal circulation. Blood Cells Mol. Dis. 2003, 30:13-21.

Kirszenbaum M, Moreau P, Teyssier M, Lafon C, Gluckman E, Dausset J, Carosella E. Evidence for the presence of the alternatively spliced HLA-G mRNA forms in human mononuclear cells from peripheral blood and umbilical cord blood. Hum. Immunol. 1995, 43(3):237-41.

Maldonado-Estrada, J., Menu, E., Rogues, P., Barre-Sinoussi, F. and Chaouat, G. Evaluation of Cytokeratin 7 as an accurate intracellular marker with which to assess the purity of human placental villous trophoblast cells by flow cytometry. J of Immunol Meth, 2004, 286: 21-34.

Masuda, J., Takayama, E., Satoh, A., Ida, M., Shinohara, T., Kojima-Aikawa, K., Ohsuzu, F., Nakanishi, K., Kuroda, K., Murakami, M., Suzuki, K. and Matsumoto, I. Levels of annexin IV and V in the plasma of pregnant and postpartum women. Thromb Haemost. 2004, 91(6):1129-36.

Oudejans C B, Tjoa M L, Westerman B A, Mulders M A, van Wijk I J, van Vugt J M. Circulating trophoblast in maternal blood. 2003, Prenat. Diagn. 23:111-116.

Tamai Y, Ishikawa T, Bösl M R, Mori M, Nozaki M, Baribault H, Oshima R G, Taketo M M. Cytokeratins 8 and 19 in the mouse placental development. J. Cell Biol. 2000, 151(3): 563-72.

Tempfer C B, Bancher-Todesca D, Zeisler H, Schatten C, Husslein P, Gregg A R., Placental expression and serum concentrations of cytokeratin 19 in preeclampsia. Obstet Gynecol. 2000, 95(5):677-82.

Troeger C, Zhong X Y, Burgemeister R, Minderer S, Tercanli S, Holzgreve W, Hahn S. Approximately half of the erythroblasts in maternal blood are of fetal origin. Mol. Hum. Reprod. 1999, 5 (12):1162-5.

van Wijk I J, Griffioen S, Tjoa M L, Mulders M A, van Vugt J M, Loke Y W, Oudejans C B. HLA-G expression in trophoblast cells circulating in maternal peripheral blood during early pregnancy. Am J Obstet. Gynecol. 2001, 184: 991-997.

Vona G, Beroud C, Benachi A, Quenette A, Bonnefont J P, Romana S, Dumez Y, Lacour B, Paterlini-Brechot P. Enrichment, immunomorphological, and genetic characterization of fetal cells circulating in maternal blood. Am. J. Pathol. 2002, 160:51-58.

Yamamoto R, Kao L C, McKnight C E, Strauss J F 3rd. Cloning and sequence of cDNA for human placental cytokeratin 8. Regulation of the mRNA in trophoblastic cells by cAMP. Mol. Endocrinol. 1990, 4(3):370-4.

---

What is claimed is:

1. A method of identifying a trophoblast in a peripheral blood cell sample of a pregnant human female, the method comprising:
   (a) contacting the peripheral blood cell sample of the pregnant human female with an anti-annexin IV antibody;
   (b) identifying cells in the peripheral blood cell sample which comprise said anti-annexin IV antibody bound thereto;
   (c) classifying said peripheral blood cell sample which comprise said anti-annexin IV antibody bound thereto as trophoblast;
   thereby identifying the trophoblast in the peripheral blood cell sample of a pregnant human female.

2. A method of isolating a trophoblast from a maternal blood sample, comprising:
   (a) identifying the trophoblast in the peripheral blood cell sample of a pregnant human female according to the method of claim 1, and
   (b) isolating the trophoblast,
   thereby isolating the trophoblast from the maternal blood sample.

3. A method of prenatally diagnosing a conceptus, comprising:
   (a) identifying in a maternal blood sample of a pregnant human female a trophoblast according to the method of claim 1, and;
   (b) subjecting said trophoblast to a conceptus diagnostic assay,
   thereby prenatally diagnosing the conceptus.

4. The method of claim 3, further comprising culturing said trophoblast prior to step (b) under conditions suitable for proliferation of said trophoblast.

5. A method of generating a trophoblast culture, comprising:
   (a) isolating trophoblasts according to the method of claim 2, and
   (b) culturing said trophoblasts under conditions suitable for proliferation of said trophoblasts,
   thereby generating the trophoblast culture.

6. The method of claim 2, wherein said isolating said trophoblast is effected by magnetic cell sorting (MACS).

7. The method of claim 2, wherein said isolating said trophoblast is effected by fluorescence activated cell sorting (FACS).

8. The method of claim 3, wherein said conceptus diagnostic assay is effected by a chromosomal analysis.

9. The method of claim 8, wherein said chromosomal analysis is effected by fluorescent in situ hybridization (FISH), primed in situ labeling (PRINS), multicolor-banding (MCB) and/or quantitative FISH (Q-FISH).

10. The method of claim 3, wherein said conceptus diagnostic assay comprises karyotype analysis.

11. The method of claim 10, wherein said karyotype analysis is performed using a staining method selected from the group consisting of G-banding, R-banding, Q-banding and C-banding.

12. The method of claim 3, wherein said conceptus diagnostic assay is effected by a DNA analysis.

13. The method of claim 12, wherein said DNA analysis comprises comparative genome hybridization (CGH) and/or identification of at least one nucleic acid substitution.

14. The method of claim 13, wherein said CGH is effected using metaphase chromosomes and/or a CGH-array.

15. The method of claim 3, wherein said diagnosing the conceptus comprises identifying at least one chromosomal and/or DNA abnormality, and/or determining a paternity of the conceptus.

16. A method of enriching for trophoblasts from a peripheral blood sample from a pregnant human subject, the method comprising:
   (a) obtaining a peripheral blood sample from a pregnant human subject;
   (b) contacting the peripheral blood sample with an antibody to annexin IV;
   (c) identifying cells in the peripheral blood sample which bind to the antibody to annexin IV; and
   (d) separating the cells identified in (c) from the blood sample to thereby enrich for the trophoblasts from the peripheral blood sample.

* * * * *